(12) United States Patent
Spenciner

(10) Patent No.: US 11,045,304 B2
(45) Date of Patent: Jun. 29, 2021

(54) DEVICE, SYSTEM, AND METHOD FOR DELIVERY OF A TISSUE FIXATION DEVICE

(71) Applicant: Medos International Sarl, Le Locle (CH)

(72) Inventor: David B. Spenciner, North Attleboro, MA (US)

(73) Assignee: Medos International Sarl, Le Locle (CH)

( * ) Notice: Subject to any disclaimer, the term of this patent is extended or adjusted under 35 U.S.C. 154(b) by 10 days.

(21) Appl. No.: 16/109,390

(22) Filed: Aug. 22, 2018

(65) Prior Publication Data

US 2018/0360593 A1    Dec. 20, 2018

Related U.S. Application Data

(62) Division of application No. 15/154,292, filed on May 13, 2016, now Pat. No. 10,085,830.

(51) Int. Cl.
*A61F 2/08* (2006.01)
*A61B 17/16* (2006.01)
(Continued)

(52) U.S. Cl.
CPC ........ *A61F 2/0811* (2013.01); *A61B 17/1637* (2013.01); *A61B 17/1714* (2013.01);
(Continued)

(58) Field of Classification Search
CPC .............. A61B 2017/00353; A61F 2002/0817
See application file for complete search history.

(56) References Cited

U.S. PATENT DOCUMENTS 4,149,277 A    4/1979  Bokros
4,682,590 A    7/1987  Kothmann
(Continued)

FOREIGN PATENT DOCUMENTS

CN    101961256 A    2/2011
CN    102481187 A    5/2012
(Continued)

OTHER PUBLICATIONS

"Extended European Search Report for Application No. 17170888.6", dated Oct. 24, 2017, 8 pages.
(Continued)

*Primary Examiner* — Jacqueline Woznicki

(57) ABSTRACT

Systems and methods for fixating a graft in a bone tunnel are provided. In general, the system includes a tissue fixation device having a delivery configuration and a deployed configuration, at least one graft retention loop coupled to the tissue fixation device, and a drill pin having a sidewall surrounding a cavity at a proximal end of the pin and at least one longitudinally oriented opening in the sidewall in communication with the cavity, the cavity being configured to fully seat the tissue fixation device. The drill pin is configured to substantially contain therein the tissue fixation device when in the delivery configuration and to enable deployment of the tissue fixation device through the opening. Drill pins configured to contain a tissue fixation device are also provided.

16 Claims, 15 Drawing Sheets

(51) Int. Cl.
*A61B 17/17* (2006.01)
*A61B 17/00* (2006.01)
(52) U.S. Cl.
CPC ........ *A61B 17/1764* (2013.01); *A61F 2/0805* (2013.01); *A61B 17/00234* (2013.01); *A61B 17/16* (2013.01); *A61B 17/1615* (2013.01); *A61B 2017/00353* (2013.01); *A61F 2/08* (2013.01); *A61F 2002/0817* (2013.01); *A61F 2002/0823* (2013.01); *A61F 2002/0829* (2013.01); *A61F 2002/0835* (2013.01); *A61F 2002/0847* (2013.01); *A61F 2002/0852* (2013.01); *A61F 2002/0876* (2013.01); *A61F 2002/0882* (2013.01); *A61M 2210/02* (2013.01)

(56) References Cited

U.S. PATENT DOCUMENTS

| | | | | |
|---|---|---|---|---|
| 5,306,301 | A * | 4/1994 | Graf | A61B 17/0401 606/151 |
| 5,484,437 | A * | 1/1996 | Michelson | A61F 2/446 606/86 A |
| 5,603,716 | A * | 2/1997 | Morgan | A61B 17/1635 128/898 |
| 5,827,289 | A * | 10/1998 | Reiley | A61B 10/025 606/86 R |
| 6,110,178 | A * | 8/2000 | Zech | A61B 17/1635 606/96 |
| 6,127,597 | A | 10/2000 | Beyar et al. | |
| 6,214,007 | B1 * | 4/2001 | Anderson | A61B 17/0401 606/304 |
| 6,290,728 | B1 * | 9/2001 | Phelps | A61B 17/3207 604/8 |
| 6,375,658 | B1 * | 4/2002 | Hangody | A61B 17/1604 606/80 |
| 6,860,901 | B1 * | 3/2005 | Baker | A61B 17/11 623/1.2 |
| 7,494,496 | B2 * | 2/2009 | Swain | A61B 17/0401 606/151 |
| 7,500,983 | B1 * | 3/2009 | Kaiser | A61B 17/0401 606/232 |
| 8,491,632 | B2 * | 7/2013 | Stone | A61B 17/0401 606/232 |
| 8,834,524 | B2 * | 9/2014 | Torrie | A61B 17/0401 24/129 R |
| 9,078,644 | B2 * | 7/2015 | Stone | A61B 17/0401 |
| 9,681,940 | B2 * | 6/2017 | Stone | A61B 17/0401 |
| 2001/0018619 | A1 * | 8/2001 | Enzerink | A61F 2/08 623/23.72 |
| 2001/0027322 | A1 * | 10/2001 | Bowman | A61B 17/0401 606/104 |
| 2002/0040241 | A1 * | 4/2002 | Jarvinen | A61F 2/0811 623/13.14 |
| 2002/0077631 | A1 * | 6/2002 | Lubbers | A61B 17/0401 606/232 |
| 2002/0082525 | A1 * | 6/2002 | Oslund | A61M 25/0169 600/585 |
| 2002/0120270 | A1 * | 8/2002 | Trieu | A61B 17/7022 623/13.11 |
| 2003/0065391 | A1 * | 4/2003 | Re | A61B 17/1714 623/13.14 |
| 2003/0088272 | A1 | 5/2003 | Smith | |
| 2004/0024403 | A1 | 2/2004 | Ellis et al. | |
| 2004/0092936 | A1 * | 5/2004 | Miller | A61B 17/1714 606/916 |
| 2004/0254609 | A1 * | 12/2004 | Esplin | A61B 17/0401 606/232 |
| 2004/0267164 | A1 * | 12/2004 | Rhodes | A61B 17/1604 600/587 |
| 2004/0267304 | A1 * | 12/2004 | Zannis | A61B 17/29 606/206 |
| 2005/0010304 | A1 * | 1/2005 | Jamali | A61F 2/2846 623/23.46 |
| 2005/0137605 | A1 * | 6/2005 | Assell | A61B 17/7074 606/96 |
| 2005/0273138 | A1 * | 12/2005 | To | A61B 17/0401 606/219 |
| 2006/0009774 | A1 * | 1/2006 | Goble | A61B 17/8875 606/85 |
| 2006/0089646 | A1 * | 4/2006 | Bonutti | A61B 17/0218 606/279 |
| 2008/0200992 | A1 * | 8/2008 | Koob | A61F 2/08 623/23.72 |
| 2008/0275554 | A1 * | 11/2008 | Iannarone | A61B 17/0401 623/13.14 |
| 2008/0294204 | A1 * | 11/2008 | Chirico | A61F 2/0805 606/327 |
| 2009/0030431 | A1 * | 1/2009 | Zaporojan | A61B 17/0469 606/139 |
| 2009/0069823 | A1 * | 3/2009 | Foerster | A61B 17/0401 606/139 |
| 2009/0182335 | A1 | 7/2009 | Struhl | |
| 2009/0216238 | A1 * | 8/2009 | Stark | A61B 17/1615 606/96 |
| 2009/0299327 | A1 * | 12/2009 | Tilson | A61M 29/02 604/500 |
| 2010/0106254 | A1 * | 4/2010 | DelSignore | A61B 17/0401 623/21.15 |
| 2010/0211075 | A1 * | 8/2010 | Stone | A61B 17/8685 606/70 |
| 2010/0241214 | A1 | 9/2010 | Holzer et al. | |
| 2010/0274355 | A1 * | 10/2010 | McGuire | A61F 2/0811 623/13.14 |
| 2010/0292792 | A1 * | 11/2010 | Stone | A61F 2/0811 623/13.14 |
| 2011/0184234 | A1 * | 7/2011 | Morgenstren Lopez | A61B 5/417 600/107 |
| 2011/0288566 | A1 * | 11/2011 | Kubiak | A61B 17/1146 606/151 |
| 2012/0059468 | A1 * | 3/2012 | Mattern | A61F 2/0811 623/13.14 |
| 2012/0116402 | A1 * | 5/2012 | Schneider | A61B 17/0401 606/80 |
| 2012/0203253 | A1 * | 8/2012 | Kubiak | A61B 17/1146 606/151 |
| 2012/0290004 | A1 * | 11/2012 | Lombardo | A61B 17/0401 606/232 |
| 2012/0293645 | A1 * | 11/2012 | Maddison | G02B 21/367 348/79 |
| 2012/0296345 | A1 | 11/2012 | Wack et al. | |
| 2013/0109910 | A1 * | 5/2013 | Alexander | A61B 17/00234 600/37 |
| 2013/0123810 | A1 | 5/2013 | Brown et al. | |
| 2013/0231667 | A1 * | 9/2013 | Taylor | A61B 17/0642 606/75 |
| 2013/0274751 | A1 * | 10/2013 | Steinwachs | A61B 17/16 606/84 |
| 2014/0067063 | A1 * | 3/2014 | Bonutti | A61F 2/441 623/13.15 |
| 2014/0194907 | A1 * | 7/2014 | Bonutti | A61B 17/8866 606/151 |
| 2014/0228898 | A1 * | 8/2014 | Gordon | A61B 17/84 606/328 |
| 2015/0020410 | A1 * | 1/2015 | Adesida | A43B 3/242 36/45 |
| 2015/0025552 | A1 * | 1/2015 | Stoll | A61F 2/0063 606/151 |
| 2015/0057750 | A1 * | 2/2015 | Timmerman | A61B 17/0401 623/13.14 |
| 2015/0073475 | A1 * | 3/2015 | Schaller | A61F 2/0811 606/232 |
| 2015/0216523 | A1 | 8/2015 | Marino et al. | |
| 2016/0051245 | A1 * | 2/2016 | Spenciner | A61B 17/0401 606/232 |
| 2016/0128683 | A1 | 5/2016 | Denham et al. | |
| 2016/0345954 | A1 * | 12/2016 | Marino | A61B 17/0401 |

(56) References Cited

U.S. PATENT DOCUMENTS

2016/0354195 A1* 12/2016 Spenciner .............. A61F 2/0811
2017/0325936 A1* 11/2017 Spenciner .............. A61F 2/0811
2018/0360593 A1* 12/2018 Spenciner .............. A61F 2/0811

FOREIGN PATENT DOCUMENTS

| | | |
|---|---|---|
| CN | 102525583 A | 7/2012 |
| CN | 104010579 A | 8/2014 |
| CN | 104135973 A | 11/2014 |
| CN | 105250049 A | 1/2016 |
| EP | 1723917 A1 | 11/2006 |
| EP | 1958591 A2 | 8/2008 |
| EP | 2777557 A1 | 9/2014 |
| FR | 2696338 A1 | 4/1994 |
| FR | 2710520 A1 | 4/1995 |
| JP | 2001198147 A | 7/2001 |
| JP | 2013158649 A | 8/2013 |
| WO | 02/065892 A2 | 8/2002 |
| WO | 2013/054354 A2 | 4/2013 |

OTHER PUBLICATIONS

U.S. Appl. No. 15/154,292, filed May 13, 2016, Device, System, and Method for Delivery of a Tissue Fixation Device.

\* cited by examiner

DEVICE, SYSTEM, AND METHOD FOR DELIVERY OF A TISSUE FIXATION DEVICE

CROSS REFERENCE TO RELATED APPLICATIONS

The present application is a divisional of U.S. patent application Ser. No. 15/154,292 entitled "Device, System, and Method for Delivery of a Tissue Fixation Device" filed May 13, 2016, which is hereby incorporated by reference in its entirety.

FIELD

Implantable tissue fixation devices as well as devices, systems, and methods for delivering such tissue fixation devices are provided.

BACKGROUND

A ligament is a piece of fibrous tissue which connects one bone to another within the body. Ligaments are frequently damaged (e.g., detached, torn or ruptured) as the result of injury or accident. A damaged ligament can impede proper stability and motion of a joint and cause significant pain. A damaged ligament can be replaced or repaired using various procedures, a choice of which can depend on the particular ligament to be restored and on the extent of the damage. When ligaments are damaged, surgical reconstruction can be necessary, as the ligaments may not regenerate on their own.

An example of a ligament that is frequently damaged as a result of injury, overexertion, aging and/or accident is the anterior cruciate ligament (ACL) that extends between a top of the tibia and a bottom of the femur. Another ligament that is often damaged and may need to be replaced is a posterior cruciate ligament (PCL). A damaged ACL or PCL can cause instability of the knee joint, arthritis, and substantial pain.

ACL reconstruction or repair typically includes the use of a tendon graft replacement procedure which usually involves drilling a bone tunnel through the tibia and up into the femur. Then a graft, which may be an artificial ligament or harvested graft, such as a tendon, is passed through a tibial portion of the tunnel (sometimes referred to as "the tibial tunnel") across the interior of the joint, and up into a femoral portion of a tunnel (sometimes referred to as "the femoral tunnel"). One end of the ligament graft can then be secured in the femoral tunnel and another end of the graft is secured in the tibial tunnel, at the sites where the natural ligament attaches.

A number of conventional surgical procedures exist for re-attaching such ligament graft to bone, which have advantages and certain drawbacks. For example, a fixation device in the form of an elongate "button," sometimes referred to as a "cortical button" can be used for an ACL fixation to the femur or tibia. However, such devices are relatively wide, such that it is required to remove a substantial amount of bone in the femur to drill a tunnel sized sufficiently to receive the device therethrough. This can complicate the surgery and extend its duration, as well as to cause inconvenience to the patient and delay healing.

Delivery of tissue fixation devices can also be difficult. For example, leading sutures that are wrapped around a tissue fixation device may break. Also, during delivery, the tissue fixation device may catch on the edge of the bone tunnel and become embedded in the bone instead of residing on top of the lateral cortex.

Accordingly, there is a need for improved tissue fixation devices and techniques for using such devices. There is also a need for improved devices, systems, and methods for delivering such tissue fixation devices.

SUMMARY

A system for delivering an implantable tissue fixation device is provided that in some embodiments includes a tissue fixation device having first and second elongate, substantially rigid support members that are discrete elements separated from each other, at least one flexible member connecting the first and second rigid support members, at least one graft retention loop coupled to the tissue fixation device, and a drill pin. The tissue fixation device has changeable dimensions such that the device has a delivery configuration and a deployed configuration. The tissue fixation device has at least one dimension that is smaller in the delivery configuration than in the deployed configuration. The drill pin has a sidewall surrounding a cavity at a proximal end of the drill pin. The cavity is configured to fully seat the tissue fixation device. The drill pin is configured to substantially contain therein the tissue fixation device when in the delivery configuration, and the drill pin is configured to enable deployment of the tissue fixation device through the opening.

The system can vary in any number of ways. For example, the drill pin can have at least one longitudinally oriented opening in the sidewall in communication with the cavity. The drill pin can have a proximal end wall in communication with the sidewall and the proximal end wall has a slot therein. The slot can be in communication with the opening and configured for passage of the at least one graft retention loop during deployment. In another example, the at least one flexible member can include a fabric.

The system can further include at least one third elongate, substantially rigid support member, and at least one second flexible member connecting the second and third rigid support members.

In some embodiments, the at least one flexible member can include a plurality of elongate connecting filaments extending between the rigid support members. The plurality of elongate connecting elements can include suture or wire. In one aspect, the rigid support members each can include a plurality of retaining elements used to couple the plurality of elongate connecting filaments to the rigid support members.

In one embodiment, the at least one graft retention loop can be coupled to the at least one flexible member and disposed around the rigid support members.

The system can further include at least one of first and second sutures removably coupled to opposite ends of the at least one flexible member. The first and second sutures can extend in opposite directions along a length of the at least one flexible member.

In some aspects, a device for delivering an implantable tissue fixation device is provided. The device includes a drill pin having a proximal end and a distal end that includes a tissue-penetrating tip, a cavity formed within the drill pin at the proximal end thereof. The cavity is defined in part by a sidewall of the drill pin. The sidewall is interrupted by a longitudinally oriented opening in communication with the cavity.

The device can vary in a number of ways. For example, the drill pin can be configured to substantially contain in the cavity an expandable tissue fixation device when in an unexpanded configuration. In another example, the drill pin can be configured to enable deployment of the tissue fixation device through the opening in the sidewall. In yet another example, the tissue fixation device can have a first and a second elongate, substantially rigid support member that are discrete elements separated from each other, and at least one flexible member connecting the first and second rigid support members.

In other aspects, a method for fixating a graft ligament into a bone tunnel is provided. The method includes forming a graft construct by coupling the graft ligament to a tissue fixation device via a graft retention loop of the tissue fixation device; inserting the tissue fixation device in a collapsed, delivery configuration into a cavity at a proximal end of a drill pin, the cavity defined by a sidewall surrounding at least part of the cavity, the cavity being configured to substantially contain the tissue fixation device therein; drilling the drill pin into a bone to form a bone tunnel; deploying the tissue fixation device through the opening in the drill pin and passing the graft construct through the bone tunnel with the tissue fixation device in the delivery configuration; and positioning the tissue fixation device over a first end of the bone tunnel in a deployed configuration. The tissue fixation device includes first and at least one second elongate, substantially rigid support members that are discrete elements separated from each other and at least one flexible member connecting the rigid support members. The tissue fixation device is positioned over a first end of the bone tunnel in a deployed configuration such that the rigid support members are spaced from one another by a distance greater than in the delivery configuration, and the graft retention loop and the graft ligament extend into the bone tunnel.

The method can have any number of variations. For example, the drill pin can have a proximal end surface in communication with the sidewall, and the proximal end surface can have a slot therein. The slot can be in communication with the opening. Prior to deployment of the tissue fixation device, the at least one graft retention loop can pass through the slot.

The method can further include pulling the drill pin through the bone tunnel. The drill pin can be pulled using a pin puller.

In some embodiments, when in the deployed configuration, the tissue fixation device can be generally perpendicular with respect to the first end of the bone tunnel. In other embodiments, the drill pin has a longitudinal axis and the tissue fixation device can be deployed through the opening at an angle with respect to the longitudinal axis. In yet other embodiments, the at least one flexible member can include a plurality of elongate connecting filaments extending between the rigid support members.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1A:
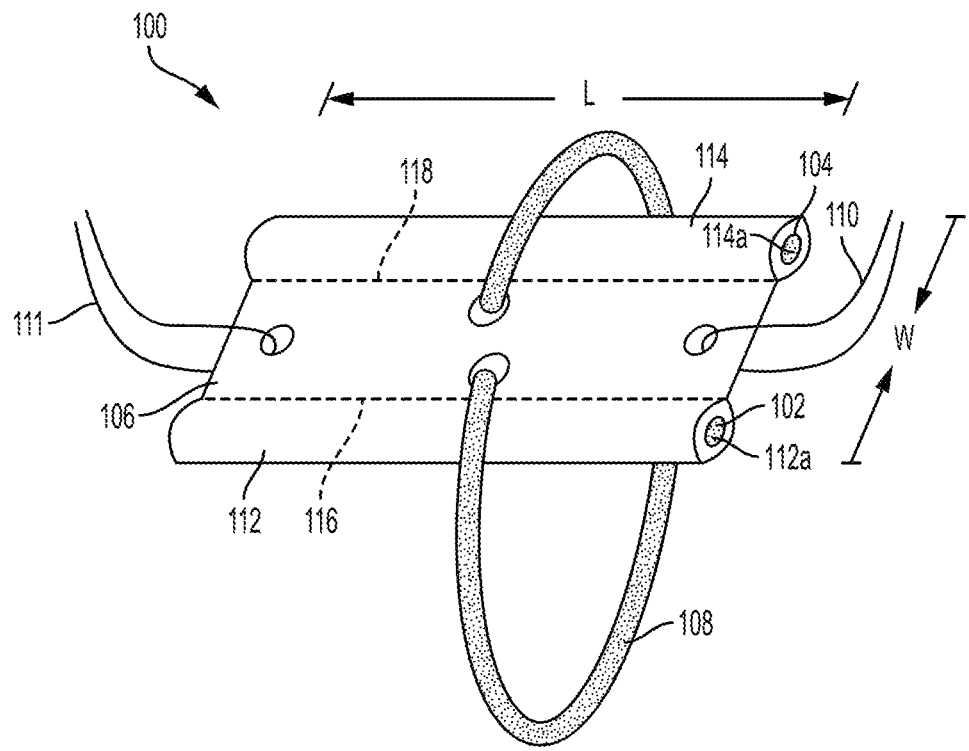
FIG. 1A is a perspective view of one embodiment of a tissue fixation device.

Certain exemplary embodiments will now be described to provide an overall understanding of the principles of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the embodiments is defined solely by the claims. Further, the features illustrated or described in connection with one exemplary embodiment may be combined with the features of other embodiments. Such modifications and variations are intended to be included within the scope of the described embodiments.

The embodiments described herein generally relate to devices, systems, and methods for fixating tendon grafts during ligament reconstruction or augmentation surgeries. The implantable tissue fixation device is one that can move between different configurations such that at least one of its dimensions can change. At the same time, the device has sufficient rigidity that allows it to withstand a load comparable to what larger devices could withstand. The system includes a drill pin that can seat the tissue fixation device during delivery. Methods of delivering the tissue fixation device using such drill pin are also provided.

Before describing the delivery system, devices, and method, we first describe exemplary tissue fixation devices to which the system and method described herein are applicable. In particular, the exemplary implantable tissue fixation device is one that includes first and second elongate, substantially rigid support members separate from one another and at least one flexible member connecting the rigid support members. The tissue fixation device further includes at least one graft retention loop coupled to the tissue fixation device and configured to retain a tissue graft in place when the device is implanted. At least one dimension of the tissue fixation device can vary. Thus, in some embodiments, prior to or following the tissue fixation device being deployed, the rigid support members can be spaced apart at a distance that is equal or approximately equal to a width of the flexible member. The flexible member, which can be a single sheet or can be in the form of one or more filaments, can also be bent, rolled, folded, crimped, or otherwise manipulated so as to decrease a distance between the rigid support members. For example, the rigid support members can be brought closer together in a delivery configuration for passing the tissue fixation device through a bone tunnel to a point of fixation. In this way, a bone tunnel having a smaller diameter, as compared to a bone tunnel diameter required to pass a conventional device, can be formed.

In the delivery configuration, the rigid support members can be disposed in a non-intersecting orientation with respect to one another. The tissue fixation device is configured such that, after it is passed through the bone tunnel, it is positioned over an opening of the tunnel such that the rigid support members are similarly disposed in the non-intersecting orientation with respect to one another.

The devices and methods described herein provide a number of advantages over existing techniques for fixating tendon grafts. For example, as mentioned above, a bone tunnel of a reduced size can be formed, which requires removing less bone from the patient's body. This can decrease a possibility of complications at the surgical site and can ultimately decrease morbidity associated with the surgical procedure. In addition, because the overall tissue fixation device is more flexible and the rigid support members can move with respect to each other, the device can be positioned against bone such that to better conform to the curved surface of the bone. In this way, the tissue fixation device can be less palpable by the patient, as compared to existing devices. Furthermore, the described tissue fixation device is simplified and it can be more cost-effective.

The described devices and methods can be used in conjunction with a variety of tendon grafts, including hamstring tendon grafts, and in a variety of different surgical contexts regardless of the type of tendon graft being used in a particular surgical procedure. The devices and methods described herein can be utilized in connection with fixating grafts for repairing or replacing ligaments in a variety of joints. In some embodiments, the devices and methods described herein have particular utility in cruciate ligament reconstruction procedures. In some embodiments, the devices and methods described herein can be utilized for fixating tendon grafts for reconstruction procedures such as, for example, the cruciate ligaments of the knee.

Figure 1B:
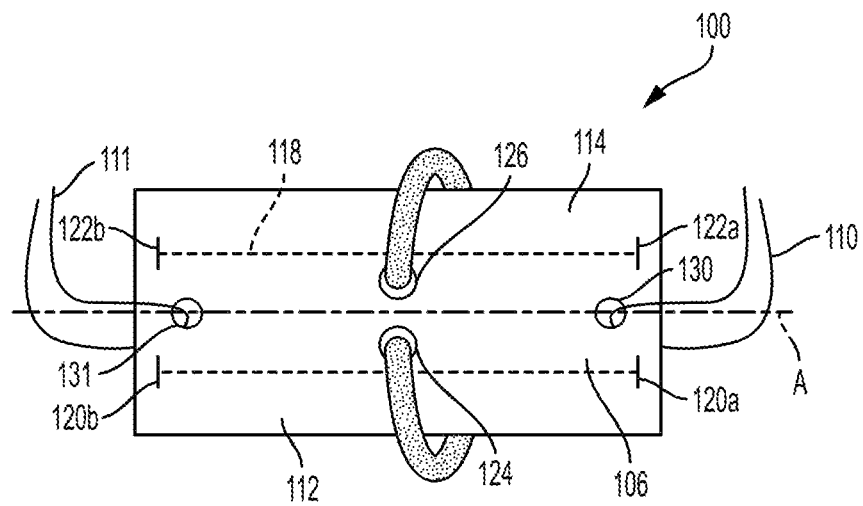
FIG. 1B is a top view of the tissue fixation device of FIG. 1A.
Figure 1C:
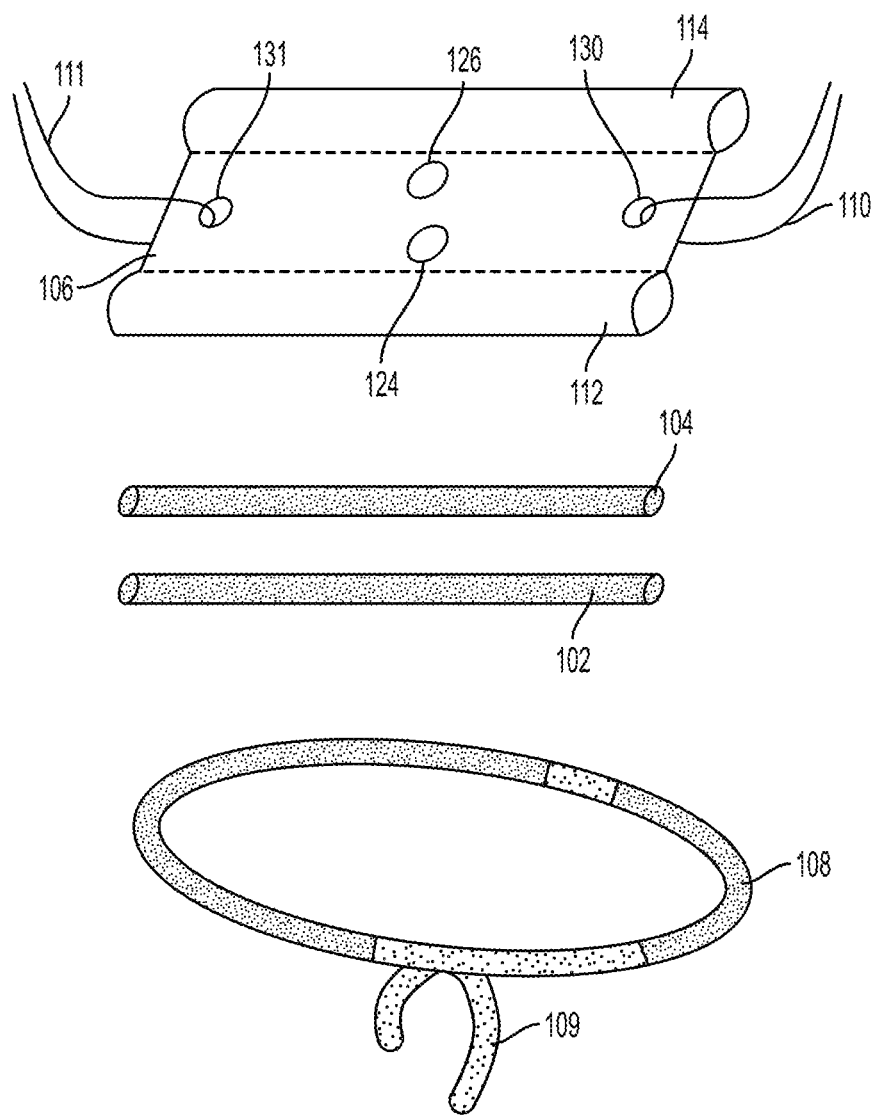
FIG. 1C is a exploded view of the tissue fixation device of FIG. 1A.

FIGS. 1A-1C illustrate one embodiment of an implantable tissue fixation device 100. The tissue fixation device 100 includes first and second substantially rigid elongate support members 102, 104, and at least one flexible member 106 connecting the first and second support members 102, 104. As shown, the tissue fixation device 100 also has at least one graft retention loop 108 coupled to the flexible member 106, as well as leading and trailing sutures 110, 111 also coupled to opposite ends of the flexible member 106. It should be appreciated that, in some embodiments, the tissue fixation device 100 can have one of the leading and trailing sutures 110, 111 rather than both the leading and trailing sutures 110, 111.

As shown in FIGS. 1A-1C, the tissue fixation device 100 in an uncompressed configuration (e.g., prior to delivery and deployment) can be generally rectangular. However, a person skilled in the art will appreciate that the tissue fixation device 100 can have any other shape. For example, in some embodiments, the tissue fixation device 100 can be square, circular or oval. The shape of the tissue fixation device 100 can be regular or irregular.

The tissue fixation device 100 has at least one changeable dimension such that the device 100 has a delivery configuration and a deployed configuration. The substantially rigid support members 102, 104 provide rigidity and structural support to the tissue fixation device 100, while the flexible member 106 is able to change its configuration to thereby allow the tissue fixation device 100 to adopt different configurations. Thus, at least one dimension (e.g., width) of the tissue fixation device 100 can be smaller in the delivery configuration than in the deployed configuration, as discussed in more detail below. Although the size of the tissue fixation device 100 in the delivery configuration, and, in some embodiments, in both the delivery and deployed configurations can be generally smaller than that of existing devices, the strength of the tissue fixation device 100 remains sufficient to withstand the load to which it is subjected.

The substantially rigid first and second support members 102, 104 can vary in a number of ways. In the illustrated embodiment, as shown in FIG. 1C, the first and second support members 102, 104 are elongate discrete elements separated from each other and that are configured to provide structural support to the tissue fixation device 100 and thus to a graft. In the illustrated embodiment, the first and second support members 102, 104 are retained within retention passages or pockets 112, 114 formed from the flexible member 106. In other embodiments, the first and second support members 102, 104 can be coupled to the at least one flexible member 106 in other ways, as discussed below.

The support members 102, 104 can be generally cylindrical such that they can have a circular or oval cross-section. It should be appreciated that the embodiments described herein are not limited to a specific configuration of the support members 102, 104. For example, the support members 102, 104 can be generally planar such that they can have a rectangular or square cross-sectional shape. Furthermore, although each of the support members 102, 104 is shown in FIG. 1C as an elongate component having no features formed therethrough or thereon, in some embodiments, each support member can have various features. For example, in some embodiments, the first and second support members can include one or more surface features (e.g., ridges, prongs or other protrusions) that facilitate coupling of the support members to the flexible member. Furthermore, in embodiments wherein the flexible member is formed from multiple elongate filaments extending between the support members, the first and second support members can include retaining features to couple such elongate filaments thereto, as described in more detail below.

The first and second support members 102, 104 can remain substantially parallel to each other in both the delivery and deployed configurations. In the illustrated embodiment, the tissue fixation device 100 is configured such that the first and second support members 102, 104 may not translate or translate only slightly relative to one another. In other words, the first and second support members 102, 104 can remain at the same position with respect to one another along a length of the tissue fixation device 100.

The size of the first and second support members 102, 104 can vary in a number of ways. For example, the length of the first and second support members 102, 104, which determines the overall length of the tissue fixation device 100, can vary depending on the requirements of an intended application. Generally, the overall length is in the range of about 5 mm to about 25 mm. In yet other embodiments, the length can vary from about 10 mm to about 15 mm. In one embodiment, the length is about 12 mm. In the illustrated embodiments, the first and second support members 102, 104 have the same length. However, it is understood that the first and second support members 102, 104 can have different lengths. A diameter of a widthwise cross-section of the first and second support members 102, 104 can vary depending on the requirements of an intended application. In one aspect, the diameter can be in the range from about 0.5 mm to about 2.0 mm. In another aspect, the diameter can be in the range of about 1.0 to about 1.1 mm. When a widthwise cross-sectional shape of the support members 102, 104 is different from circular or oval, the size of the cross-section is similar to the above.

The first and second support members 102, 104 can be formed from any suitable material, and the individual members need not be formed from the same material. For example, they can be formed from a surgical stainless steel, titanium alloy, or another biocompatible, sufficiently strong metal that allows the first and second support members 102, 104 to withstand the load to which they will be subjected. In some embodiments, the first and second support members 102, 104 are formed from a Chromium Molybdenum (Co—Mo) alloy. The first and second support members 102, 104 can also be formed from non-metallic materials, which may be or may not be biodegradable materials. Non-limiting examples of such non-metallic materials include a polyether ether ketone (PEEK), polylactic acid (PLA), biphasic tricalcium phosphate (bTCP), and Biocryl® Rapide® material composed of 30% osteoconductive β-TCP and 70% polylactide co-glycolide (PLGA). In some embodiments, the first and second support members 102, 104 can be formed from ceramics, such as, for example, aluminum oxide. The first and second support members 102, 104 can be formed from one material or a combination of two or more materials. The materials typically have a high strength such that the Ultimate Tensile Strength is about 500 MPa and the Yield Strength is about 215 MPa. However, the materials can be such that their Ultimate Tensile Strength and the Yield Strength can have other values. The materials used to form the first and second support members 102, 104 can be such that the tissue fixation device 100 has a yield load in bending that varies from about 250 Newton (N) to about 2500 N, depending on a specific application. In one embodiment (e.g., in which the tissue fixation device 100 is used for an ACL replacement procedure), the yield load in bending of the tissue fixation device 100 can be about 1000 N.

The form and structure of the flexible member 106 connecting the first and second support members 102, 104 can vary in a number of ways. In the illustrated embodiment, as shown in FIG. 1A-1C, the flexible member 106 is in the form of a fabric sheet. However, in some embodiments, the flexible member 106 can be in the form of elongate connecting filaments extending between the rigid support members, as discussed in more detail below. Regardless of its specific configuration, the flexible member can be manipulated so as to change its configuration to thereby decrease a distance between the first and second support members 102, 104. In the illustrated embodiment, the flexible member 106 in the form of the fabric sheet can be rolled, bent, folded, collapsed, crimped, or otherwise manipulated so that a distance between the first and second support members 102, 104 can be decreased. In this way, a width of the tissue fixation device 100 can decrease. In such a configuration, the tissue fixation device 100 can be passed through a bone tunnel having a diameter that is less than a diameter that would be required to pass a conventional tissue fixation device therethrough.

The flexible member 106 can connect the first and second support members 102, 104 such that a distance at which the first and second support members 102, 104 are spaced apart is changeable in a number of ways. As shown in FIGS. 1A-1C, in the illustrated embodiment, the flexible member 106 has first and second retaining passages or pockets 112, 114 formed on either side of a longitudinal axis A of the tissue fixation device and which are configured to retain the first and second support members 102, 104 therein. It should be appreciated that FIG. 1A shows the first and second support members 102, 104 visible at the openings 112a, 114a of the first and second pockets 112, 114 for illustration purposes only. It is understood, however, that both openings of each of the pockets 112, 114 can be closed or closeable. In this way, the first and second support members 102, 104 are unable to slide out of the pockets 112, 114.

In the illustrated embodiment, the first and second pockets 112, 114 are formed by configuring the fabric forming the flexible member 106. For example, longitudinal sides of the fabric (which can be rectangular or square) can be rolled or folded towards a mid-portion of the fabric (which is also a mid-portion of the flexible member 106), and the folds can be stitched or otherwise secured to the remainder of the fabric to thereby form the longitudinal pockets. As shown in FIGS. 1A-1C, longitudinal stitches 116, 118 are formed at a distance spaced apart from opposite sides of the flexible member 106 to form the pockets 112, 114, respectively. In addition, transverse stitches 120a, 120b are formed to retain the first support member 102 within the first pocket 112, and transverse stitches 122a, 122b are formed to retain the second support member 104 within the second pocket 114. However, it should be appreciated that the first and second pockets 112, 114 can be formed in other ways, as embodiments described herein are not limited to a specific way of forming the pockets or otherwise retaining the support members. For example, the flexible member 106 can be manufactured such that it can have the pockets 112, 114 or other retaining features preformed and configured to receive and hold therein the first and second support members 102, 104.

Forming the pockets can involve placing the first and second support members 102, 104 at opposite longitudinal sides of the fabric and rolling or folding the sides of the fabric over the support members 102, 104, so as to enclose the support members 102, 104. Alternatively, the support members 102, 104 can be inserted into the pockets after the pockets are formed. Regardless of the specific way of forming the pockets, the first and second support members 102, 104 can each be held tightly within a respective pocket.

The flexible member can connect the first and second support members in other ways as well. For example, in some embodiments, the flexible member 106 can include a plurality of slits, holes or other openings along longitudinal sides thereof. To couple the first and second support members to one another, the flexible member can be passed through the openings, e.g., by entering the openings at alternating sides of the flexible member 106. Additionally or alternatively, as mentioned above, the first and second support members can include one or more surface features (e.g., ridges, prongs or other protrusions) that can facilitate interlocking between the support members and the flexible member. The first and second support members can be coupled to the flexible member in any other manner, such that the first and second support members do not separate from the flexible member during delivery and deployment of the device, and after the device is implanted.

The flexible member 106 can have various sizes and are dimensions (including length, width and thickness) and a person skilled in the art can readily determine the appropriate size depending on the requirements of a given application. The width (W) of the flexible member 106 in the uncompressed configuration of the tissue fixation device 100 (before delivery and deployment of the device 100) is shown in FIG. 1A and the width can range from about 2 mm to about 8 mm. In one embodiment, the width can be about 5 mm. The length (L) of the flexible member 106 shown in FIG. 1A can depend on the length of the first and second support members 102, 104. Thus, the flexible member 106 can be long enough to retain the first and second support members 102, 104 in the retaining pockets 112, 114. For example, the length (L) of the flexible member 106 can vary from about 5 mm to about 28 mm. In some aspects, the length can vary from about 10 mm to about 18 mm. In some aspects, the length can vary from about 12 mm to about 13 mm. In one aspect, the length (L) can be about 12 mm.

The flexible member 106 can be made from a number of suitable materials, such as biologically inert and biocompatible fabrics. For example, the flexible member 106 can be manufactured from fabrics such as polyethylene terephthalate (Dacron®) or polytetrafluoroethylene (PTFE, or GORE-TEX®). Alternatively, the flexible member 106 can be made from resorbable plastic fibers such as, for example, polylactic acid (PLA).

Referring back to FIGS. 1A-1C, as mentioned above, the tissue fixation device 100 includes the graft retention loop 108 coupled thereto. The graft retention loop 108 is configured (in size, shape and strength) to hold a tissue graft passed through the loop when the tissue fixation device 100 is implanted. In the illustrated embodiment, the graft retention loop 108 is coupled to the flexible member 106 and disposed around the rigid support members 102, 104. The graft retention loop 108 can be coupled to the flexible member 106 by passing therethrough. As shown in FIG. 1C, the graft retention loop 108 can be formed from a suture or a similar material having its opposite free ends coupled together at a knot 109. It should be appreciated that, the knot 109 can be formed after the suture is passed through the flexible member 106. It should also be appreciated that the graft retention loop 108 can be coupled to the flexible member 106 using techniques that may not involve forming a knot. For example, the loop can be a continuous loop, or the ends of the suture forming the loop can be joined together using a lap joint, splice joint, or other technique. Additionally or alternatively, the ends of the suture can be glued together. Any other technique can be used as embodiments are not limited in this respect.

The graft retention loop 108 can have any suitable dimensions. In some embodiments, it can have a length (before forming a loop) in the range of about 10 mm to about 60 mm. In some embodiments, the length can range from about 15 mm to about 25 mm. In one embodiment, the length can be about 15 mm. The length of the graft retention loop 108 can be fixed. Alternatively, in some embodiments, the length of the graft retention loop 108 can be adjustable such that it can be changed by a user when the tissue fixation device 100 is in use. For example, the graft retention loop 108 can be manipulated to increase its length when a longer loop is desired. As another example, a length of the graft retention loop 108 can be decreased if the uncompressed length is longer than desired.

The thickness (diameter) of the material forming the loop can also vary and it is typically in the range from about 1 mm to about 4 mm. Also, the graft retention loop 108 can be formed from any suitable material(s) and it can be formed in a number of ways. For example, it can be a continuous loop or it can be braided, woven, or otherwise formed construct. A person skilled in the art will appreciate that any variety of materials (including ultra-high-molecular-weight polyethylene (UHMWPE)) can be used to form the loop, including those typically used to form sutures. Further, the tensile strength at break can be about 50 MPa and the tensile strength at yield can be about 20 MPa such that the material is sufficiently strong to serve its intended purpose of graft retention. The maximum tensile load of the entire construct can be in the range from about 250 N to about 2500 N. It should be appreciated that the described embodiments are not limited to any specific graft retention loop.

The graft retention loop 108 can be formed from any suitable materials. For example, the loop 108 can be formed from a suture that can be any type of suture. For example, the suture can be from size 0 to size 5, such as Orthocord® suture or Ethibond® suture. In some embodiments, the suture can be formed from ultra-high-molecular-weight polyethylene (UHMWPE). In some embodiments, the suture can include high-molecular weight-polyethylene (HMWPE) or HMWPE with a co-braid (e.g., monofilament polypropylene, nylon or other co-braid). In some embodiments, monofilament sutures such as, for example, Monocryl® available from Ethicon, Inc., may be utilized. As another example, an absorbable suture such as Vicryl® (a copolymer made from 90% glycolide and 10% L-lactide) also available from Ethicon, Inc. may be used. The sutures used herein can have any suitable amount and type of bioabsorbable material, which can depend on a particular surgical procedure and/or surgeon preferences.

As shown in FIGS. 1A-1C, the flexible member 106 includes apertures or openings 124, 126, formed at opposite sides of the longitudinal axis A of the flexible member 106, and these are intended for passing the graft retention loop 108 therethrough so as to couple the loop 108 to the tissue fixation device 100. The openings 124, 126 can be pre-formed or they can be formed as a suture forming the graft retention loop 108 is passed through the flexible member 106. The openings 124, 126 can be reinforced by additional sutures placed around their perimeter, or in any other manner, so as to prevent fabric forming the flexible member 106 from fraying and improve the rigidity of the openings.

It should be appreciated that the two openings 124, 126 formed through the flexible member 106 are shown by way of example only, as a single openings can be formed. As another example, the loop 108 can wrap around the tissue fixation device 100, without passing through the flexible member. In some embodiments, a tissue fixation device can include a graft retention loop can be formed from a flexible member. For example, the flexible member can be tied to form a loop and it can be otherwise configured into a loop-like shape.

The tissue fixation device 100 also includes leading and trailing sutures 110, 111 that assist in passing the device 100 through the bone tunnel and in "flipping" device 100 (i.e., transferring the device 100 from a delivery configuration to a deployed configuration) after it is passed through the tunnel, as discussed in more detail below. The leading and trailing sutures 110, 111 can have any suitable length and can be formed from any suitable materials. For example, in some embodiments, the leading suture 110 can be formed from ultra-high-molecular-weight polyethylene (UHWMPE) high strength Orthocord® suture size 5, and the trailing suture 111 can be formed from ultra-high-molecular-weight polyethylene (UHWMPE) high strength Orthocord® suture size 2. In some embodiments, one or both of the leading and trailing sutures can be from size 0 to size 5, such as Orthocord® suture commercially available from DePuy Mitek, and Ethibond® suture available from Ethicon, Inc. However, a person skilled in the art will appreciate that the leading and trailing sutures 110, 111 can be formed from any suitable materials, including from the same type of suture.

The leading and trailing sutures 110, 111 can be coupled to the tissue fixation device 100 in a number of ways. In the illustrated embodiment, as shown in FIGS. 1A-1C, the flexible member 106 includes apertures or openings 130, 131 for passing the leading and trailing sutures 110, 111 therethrough. As shown, the openings 130, 131 are formed at opposite sides thereof and disposed approximately along the longitudinal axis A of the flexible member 106. Like openings 124, 126 for retaining the loop 108, the openings 130, 131 can be pre-formed in the flexible member 106 or they can be formed as the leading and trailing sutures 110, 111 are passed through the flexible member 106 (e.g., using a needle). The openings 130, 131 can be reinforced in a suitable manner. Alternatively, the leading and trailing sutures can pass through a single aperture or opening.

Figure 2A:
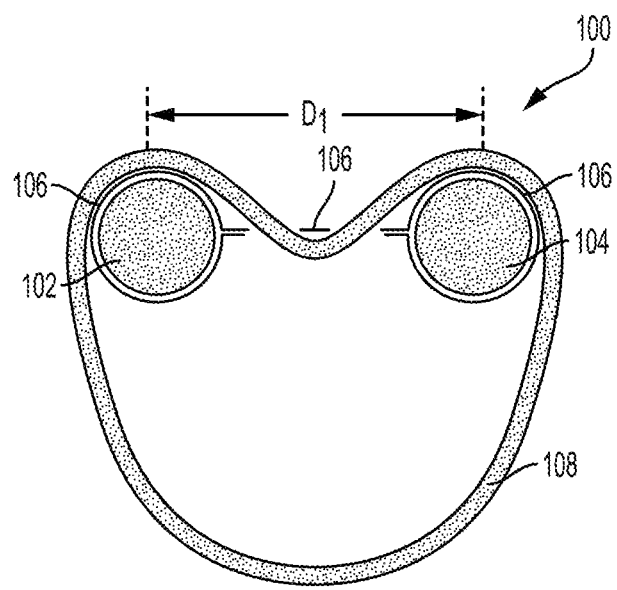
FIG. 2A is a side cross-sectional view of the tissue fixation device of FIG. 1A in an uncompressed configuration.
Figure 2B:
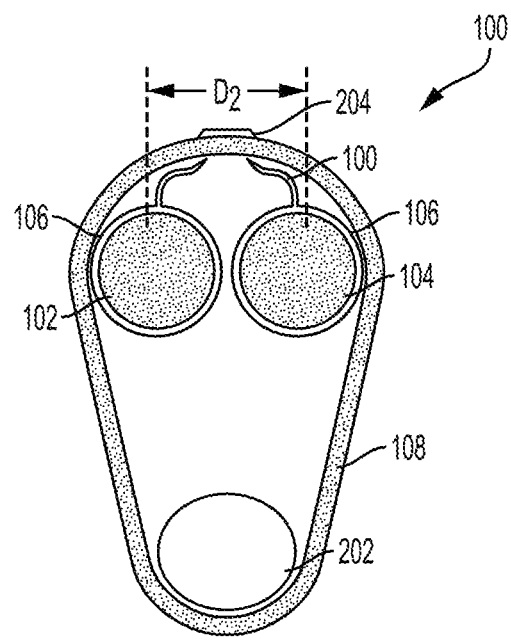
FIG. 2B is a side cross-sectional view of the tissue fixation device of FIG. 2A in a compressed configuration.

As indicated above, the tissue fixation device 100 is configured such that the flexible member 106 can be folded, crimped, compressed, or otherwise deformed and the distance between the rigid support members 102, 104 can thus decrease relative to the original (undeformed or uncompressed) configuration of the device to facilitate delivery. FIGS. 2A and 2B illustrate the tissue fixation device 100 in an original, uncompressed configuration (FIG. 2A) and in a compressed configuration (FIG. 2B), which can be a deployed and/or delivery configuration. As shown, in the original, uncompressed configuration, the rigid support members 102, 104 can be disposed such that a distance D1 between their mid-points is greater than a distance D2 between the mid-points in the compressed configuration. The tissue fixation device 100 can be passed through a bone tunnel in the compressed delivery configuration in which the rigid support members 102, 104 maintained in a non-intersecting orientation with respect to one another, as shown in FIG. 2B. In the delivery configuration, the rigid support members 102, 104 are disposed close to each other such that the tissue fixation device 100 can be passed through a bone tunnel having a reduced diameter.

After the tissue fixation device 100 is passed through the bone tunnel, as discussed in more detail below, it is placed over an opening in a bone tunnel (not shown) in the compressed deployed configuration such that the graft retention loop 108 is used to retain a tissue graft 202. Thereafter, the device can be rearranged in a manner desired by the surgeon. Typically, because the tissue graft 202 is tensioned due to load applied thereto such that the graft retention loop 108 extends into the bone tunnel, the rigid support members 102, 104 tend to be brought closer together as the flexible member 106 forms one or more folds 204. As the rigid support members 102, 104 come closer together, they are maintained in a non-intersecting orientation with respect to one another. It should be appreciated that, in the delivery configuration, the rigid support members 102, 104 can be positioned closer to one another as compared to their relative positions in the original, uncompressed configuration. Thus, a distance between the mid-points of the rigid support members 102, 104 in the delivery configuration can be equal or greater than D2 and less than D1. However, in some embodiments, in the delivery configuration, the rigid support members 102, 104 can be positioned with respect to one another such that a distance between their mid-points is approximately equal to the distance D1 in the uncompressed configuration of the tissue fixation device 100.

Figure 3A:
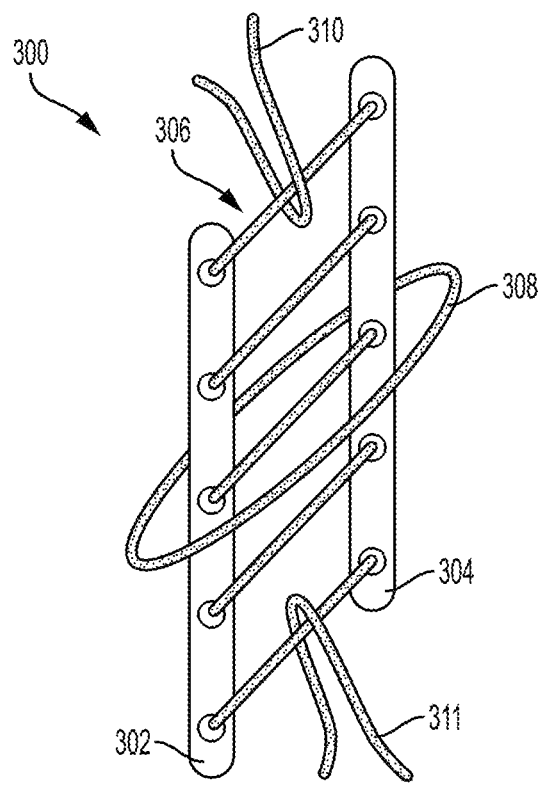
FIG. 3A is a plan view of another embodiment of a tissue fixation device in an undeployed configuration prior to the device being passed through a femoral tunnel.
Figure 3B:
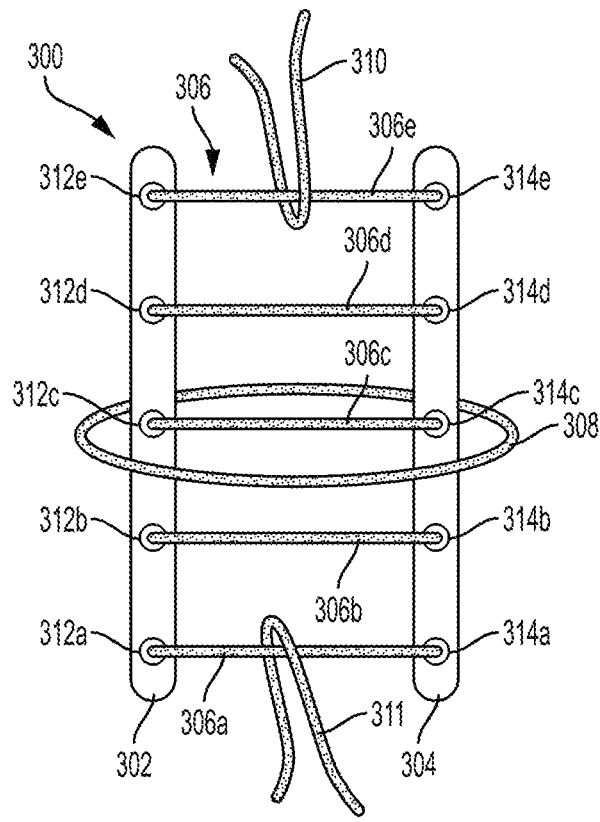
FIG. 3B is a perspective view representative of the tissue fixation device of FIG. 3A in a deployed configuration after the device is passed through a femoral tunnel.

FIGS. 3A and 3B illustrate another embodiment of a tissue fixation device 300 including first and second substantially rigid support members 302, 304 and a flexible member 306 in the form of a plurality of elongate connecting filaments 306a-306e extending between the rigid support members 302, 304. Like tissue fixation device 100 (FIGS. 1A-1C), the tissue fixation device 300 also includes a graft retention loop 308 coupled thereto such that it passes around both sides of the device, and leading and trailing sutures 310, 311 also coupled thereto.

The first and second rigid support members 302, 304 are substantially elongate elements coupled to one another via the flexible member 306 such that a distance between the support members 302, 304 is changeable. Each of the rigid support members 302, 304 can include a plurality of retaining elements used to couple the elongate connecting filaments 306a-306e thereto. Thus, as shown in FIGS. 3A and 3B, the first support member 302 includes first retaining elements 312a-312e, and the second support member 304 includes second retaining elements 314a-314e. In the illustrated embodiment, the first and second retaining elements 312a-312e, 314a-314e are in the form of openings formed in the rigid support members 302, 304 and longitudinally spaced along a length of the support members 302, 304. The first retaining elements 312a-312e can be spaced the same distance apart along the first support member 302, and the second retaining elements 314a-342e can be similarly spaced the same distance apart along the second support member 304.

The openings can have a round or oval cross-sectional shape, and they can be formed such that, in the uncompressed configuration, an opening in one of the support members is disposed opposite to an opening in another one of the support members. A person skilled in the art will appreciate, however, that the retaining elements 312a-312e, 314a-314e can be formed in the rigid support members 302, 304 in other manners, as embodiments are not limited in this respect. Furthermore, retaining elements having other configurations (e.g., hooks, protrusions or other structures) can be formed on or within the support members 302, 304.

The first and second rigid support members 302, 304 can be sized and constructed similar to first and second rigid support members 102, 104 (FIGS. 1A-1C), as discussed above. Also, the first and second rigid support members 302, 304 can be formed from materials similar to those used to form the first and second rigid support members 102, 104 which are also discussed above.

In the illustrated embodiment, the elongate connecting filaments 306a-306e connecting the first and second rigid support members 302, 304 can each be formed from a separate element (e.g., suture or wire) such that the tissue fixation device 300 has an overall "ladder-like" configuration. However, in some embodiments, a single suture or wire element can be passed through the retaining elements 312a-312e, 314a-314e or coupled to via other retaining elements to the rigid support members 302, 304. The single suture can be used to form a tissue fixation device having "ladder-like" configuration or a tissue fixation device in which elongate connecting filaments from a crisscrossed pattern between the support members.

The connecting filaments 306a-306e can be rigid such that, in a delivery configuration, the distance between the rigid support members 302, 304 can decrease as they translate with respect to each other, as shown in FIG. 3B. In embodiments in which the connecting filaments 306a-306e are formed from a flexible suture, wire, or other material(s), the connecting filaments 306a-306e can be compressed in a manner similar to flexible member 206 (FIGS. 2A and 2B) to allow the rigid support members 302, 304 to come closer together without translating with respect to each other.

As mentioned above, the connecting filaments 306a-306e of the flexible member 306 can be formed from a suture or wire. The suture can be any type of suture. For example, the suture can be from size 0 to size 5, such as Orthocord® suture or Ethibond® suture. In some embodiments, the suture can be formed from ultra-high-molecular-weight polyethylene (UHMWPE). In some embodiments, the suture can include high-molecular weight-polyethylene (HMWPE) or HMWPE with a co-braid (e.g., monofilament polypropylene, nylon or other co-braid). In some embodiments, monofilament sutures such as, for example, Monocryl® available from Ethicon, Inc., may be utilized. As another example, an absorbable suture such as Vicryl® (a copolymer made from 90% glycolide and 10% L-lactide) also available from Ethicon, Inc. may be used. The sutures used herein can have any suitable amount and type of bioabsorbable material, which can depend on a particular surgical procedure and/or surgeon preferences. In embodiments in which the connecting filaments 306a-306e are formed from a wire, the wire can be formed from surgical stainless steel, titanium alloy, or other biocompatible metal, or polymer.

As shown in FIGS. 3A and 3B, the graft retention loop 308 can be coupled to the tissue fixation device 300 by being disposed around the rigid support members 302, 304. The graft retention loop 308 can additionally or alternatively be coupled to the rigid support members 302, 304 in a number of other ways. For example, the graft retention loop 308 can be coupled to a feature (not shown) formed on or in one or both of the support members 302, 304. As another example, the graft retention loop 308 can be coupled to the rigid support members 302, 304 by passing around or through one of the flexible connecting filaments 306a-306e, for example, around or through the filament 306c or one or more of other filaments.

The leading and trailing sutures 310, 311 can be coupled to the tissue fixation device 300 in a number of ways. For example, the leading and trailing sutures 310, 311 can pass around one or more of the elongate connecting filaments 306a-306e. Thus, in the illustrated embodiment, as shown in FIGS. 3A and 3B, the leading and trailing sutures 310, 311 are coupled to the tissue fixation device 300 such that the leading suture 310 passes (e.g., loops) around the connecting filament 306e at one end of the device 300 and the trailing suture 311 passes (e.g., loops) around the connecting filament 306a at the opposite end of the device 300. It should be appreciated that the locations of the leading and trailing sutures can be reversed such that the leading suture 310 passes around the connecting filament 306a and the trailing suture 311 passes around the connecting filament 306e. Furthermore, as a person skilled in the art will appreciate, the leading and trailing sutures 310, 311 can be coupled to the tissue fixation device 300 in other ways. For example, one or both of the leading and trailing sutures 310, 311 can pass through one or more of the elongate connecting filaments 306a-306e. Also, the leading and trailing sutures can loop more than one time about one or more of the elongate connecting filaments 306a-306e.

The leading and trailing sutures 310, 311 can be formed from materials similar to those used to form leading and trailing sutures 110, 111 of tissue fixation device 100 (FIGS. 1A-1C), as discussed above.

Figure 4:
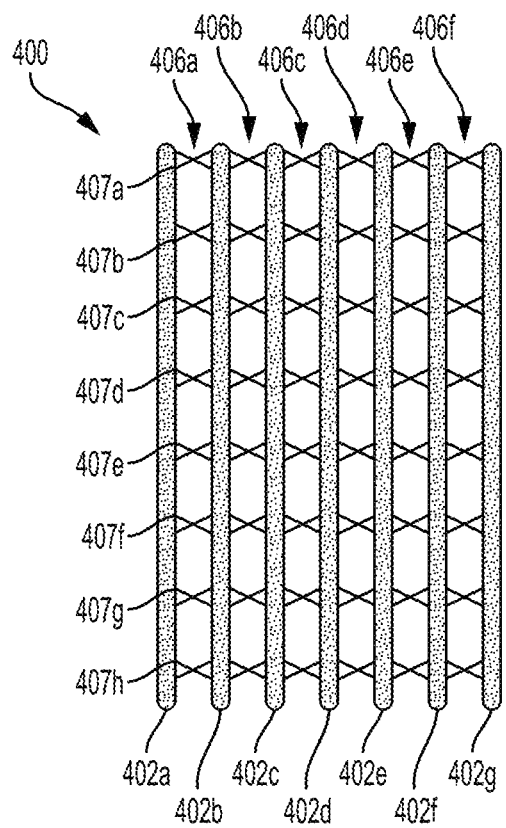
FIG. 4 is a perspective view of an embodiment of a tissue fixation device including multiple rigid support members.

In some embodiments, a tissue fixation device has more than two rigid support members. In such embodiments, the rigid support members can have a reduced diameter such that the tissue fixation device can move to a compressed configuration by being rolled into a tube-like configuration. FIG. 4 illustrates an implantable tissue fixation device 400 that includes a plurality of substantially rigid elongate support members 402a-402g and a plurality of flexible members 406a-406f each connecting two of the support members 402a-402g. Although not shown, the tissue fixation device 400 also has at least one graft retention loop (which can be similar to graft retention loop 108 of FIGS. 1A-1C) coupled to one or more of the flexible members 406a-406g in a suitable manner. The tissue fixation device 400 can also have one or both of leading and trailing sutures coupled to opposite ends thereof.

As mentioned above, the rigid support members 402a-402g can have a small diameter, for example, about 0.1 mm. It should be appreciated that seven rigid support members 402a-402g are shown in FIG. 4 by way of example only, since the tissue fixation device 400 can have other number of rigid support members (e.g., three, four, five, six, eight or more than eight). The larger the number of the rigid support members, the smaller the diameter of each of the rigid support members. The rigid support members 402a-402g are connected to each other via flexible members 406a-406g such that the rigid support members 402a-402g remain in a non-intersecting orientation with respect to one another in uncompressed and compressed configurations.

As shown in FIG. 4, each of the flexible members 406a-406g connecting respective two of the rigid support members 402a-402g includes multiple filaments. For example, the flexible member 706a can be in the form of a plurality of filaments 407a-407h as shown in FIG. 4. In the illustrated embodiment, the filaments 407a-407h can be spaced at approximately equal distances away from each other along a length of the rigid support members 402a-402g. However, the filaments 407a-407h can be disposed along a length of the rigid support members 402a-402g at other intervals.

As shown, each of the filaments 407a-407h can include one or more elements movably coupled to each other. In the illustrated embodiment, each of the filaments is in the form of two triangular-shaped elements connected to one another so as to form a cross-hatching pattern. The filaments can also be formed by interconnected rings or any other elements. It should be appreciated that eight filaments 407a-407h together forming a flexible member are shown in FIG. 4 by way of example only, as the rigid support members 402a-402g can be coupled to one another using any suitable number of any other type(s) of filaments. The filaments can be formed from a metal, fabric or any other material.

The support members 402a-402g are connected via the flexible members 406a-406g such that adjacent support members can be displaced with respect to each other. The support members 402a-402g can be connected via the flexible members 406a-406g such that the support members 402a-402g at least partially restricted from translating with respect to one another. Alternatively, the flexible members 406a-406g can connect the support members 402a-402g such that adjacent support members 402a-402g can be translated with respect to one another.

The tissue fixation device 400 can move from an uncompressed to a compressed configuration by being rolled into a tube-like configuration. In such configuration, the tissue fixation device 400 can be passed through a bone tunnel (e.g., a femoral tunnel) having a relatively small diameter. For example, the tissue fixation device 400 can be passed in the compressed configuration through a femoral socket and a passing tunnel which will be discussed in more detail with respect to FIGS. 18 and 19A-G. After the tissue fixation device 400 passes through the bone tunnel, the device 400 can be moved to an uncompressed or partially uncompressed configuration to support the tissue fixation loop and a graft coupled thereto. For example, the tissue fixation device 400 can be unrolled into a flat or partially flat configuration.

Figure 5:
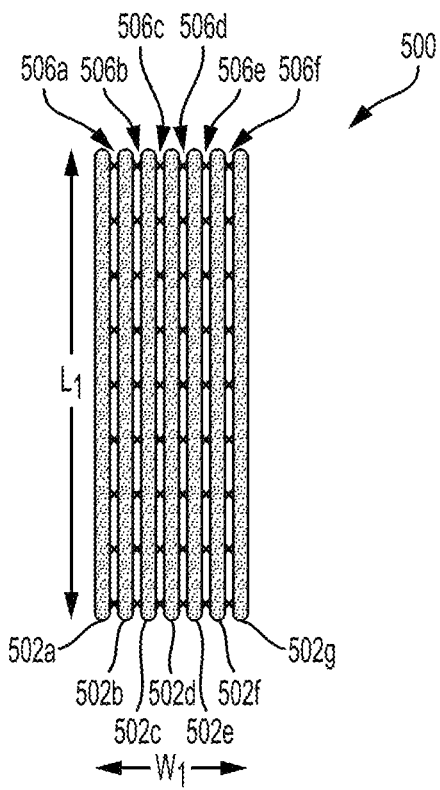
FIG. 5 is a perspective view of another embodiment of a tissue fixation device including multiple rigid support members.

FIG. 5 illustrates another embodiment of a tissue fixation device 500 which is similar to tissue fixation device 400 (FIG. 4). As shown, the tissue fixation device 500 includes a plurality of substantially rigid elongate support members collectively referred to as rigid elongate support members 502 and a plurality of flexible members each connecting two of the support members 502 and collectively referred to as flexible members 506. The flexible members 506 can be similar to the flexible members 406a-406g (FIG. 4) or they can have other configuration.

In the illustrated embodiment, as shown in FIG. 5, a distance between each adjacent support members 502 can be relatively small. The width (W1 in FIG. 5) of the tissue fixation device 500 in the uncompressed configuration (before delivery and deployment of the device 500) can range from about 2 mm to about 8 mm. In one embodiment, the width can be about 5 mm. The length (L1 in FIG. 5) of the tissue fixation device 500 can depend on the length of the rigid elongate support members 502 and it can vary from about 5 mm to about 28 mm. In some embodiments, the length L1 can vary from about 10 mm to about 18 mm. In some embodiments, the length can vary from about 12 mm to about 13 mm. In one embodiment, the length L1 can be about 12 mm. A width of each of the flexible members 506 can depend on a diameter of the support members 402a-402g. For example, in embodiments in which the diameter of each of the support members 702a-702g is about 0.1 mm, the width of each of the flexible members 506 can vary from about 0.03 mm to about 0.08 mm.

Figure 6A:
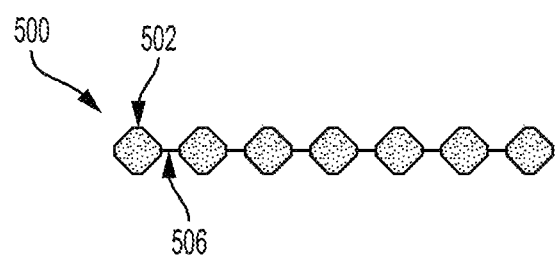
FIG. 6A is a schematic side view of the tissue fixation device of FIG. 5 in an uncompressed configuration.
Figure 6B:
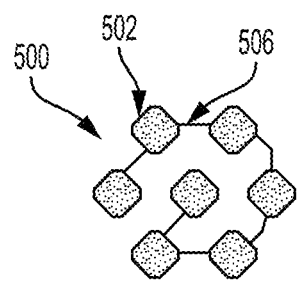
FIG. 6B is a schematic side view of the tissue fixation device of FIG. 5 in a compressed configuration.

FIG. 6A shows the tissue fixation device 500 in an uncompressed configuration, and FIG. 6B shows an exemplary embodiment of the tissue fixation device 500 in a compressed (rolled-up) configuration. The tissue fixation device 500 can be delivered to an implantation site in such a configuration.

Figure 6C:
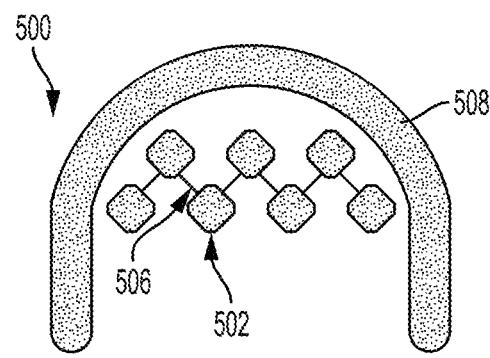
FIG. 6C is a schematic side view of the tissue fixation device of FIG. 5 having a load applied thereto.

FIG. 6C illustrates the tissue fixation device 500 in the deployment configuration, with a graft retention loop 508 coupled thereto in a suitable manner. As shown in FIG. 6C, because a tissue graft (not shown) coupled to the graft retention loop 508 is tensioned due to load applied thereto, the rigid support members 502 tend to be brought closer together as the flexible members 506 allow the rigid support members 502 to be replaced with respect to one another. Thus, in such configuration, the tissue fixation device 500 is no longer in the rolled-up into a tube and, at the same time, the device 500 has a configuration different from a fully flattened configuration, as shown in FIG. 6B. A person skilled in the art will appreciate that the tissue fixation device 500 is shown in FIGS. 6B and 6C by way of example only and that the tissue fixation device 500 can be compressed in different other ways in its deployment and delivery configurations.

Tissue fixation devices of the type described above can be implanted according to various techniques. Particularly useful techniques are described in U.S. patent application Ser. No. 14/730,484, entitled "Tissue Fixation Device," which is hereby incorporated by reference in its entirety. Additional devices, systems, and methods for delivering an implantable tissue fixation device are described below.

In one aspect, a suitable delivery device generally includes a drill pin having a proximal end and a distal end that includes a tissue-penetrating tip. A cavity is formed within the drill pin, such as at the proximal end thereof. The cavity is defined in part by a sidewall of the drill pin and the sidewall is interrupted by a longitudinally oriented opening in communication with the cavity. The drill pin is configured to substantially contain in the cavity an expandable tissue fixation device (such as one of the type described above), which can be housed in the cavity in an unexpanded or delivery configuration. In some embodiments, the cavity is configured to fully seat the tissue fixation device. Further, the drill pin is configured to enable deployment of the tissue fixation device through the opening. The delivery system generally includes a tissue fixation device such as described herein, at least one graft retention loop coupled to the tissue fixation device, and a drill pin having a cavity configured to seat the tissue fixation device therein. Methods of fixating a graft ligament into a bone tunnel using such devices and systems are also provided and are discussed below.

The disclosed devices, systems, and methods for delivering a tissue fixation device have a number of advantages. For example, fewer surgical steps, such as reaming steps, are required when using the drill pin described herein, and the tissue fixation device can be deployed during the drilling step. As another example, a surgeon has more control when pulling the tissue fixation device through the bone tunnel because the tissue fixation device is seated in a drill pin and is thus not susceptible to being caught on the bone tunnel wall during deployment. As such, the deployment location of the drill pin is more certain. Tissue fixation device delivery can also be effected in a more controlled manner because instead of winding suture around a pair of forceps, a pin pusher can be used to pull the drill pin along with the tissue fixation device and graft retention loop through the bone tunnel.

Figure 7A:
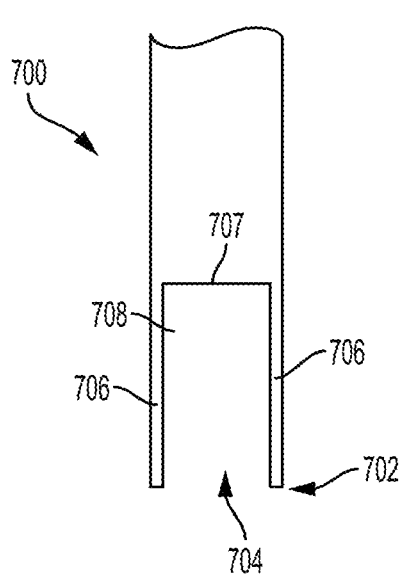
FIG. 7A is a partial side view of an embodiment of a drill pin having an opening in a sidewall thereof.
Figure 7B:
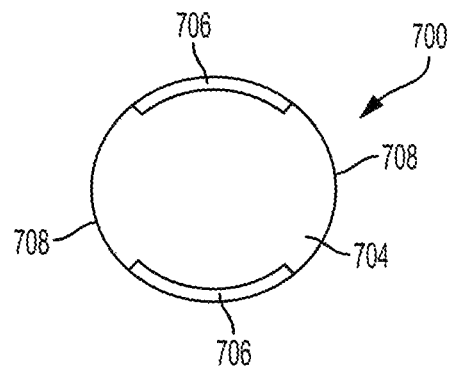
FIG. 7B is an end view of the drill pin of FIG. 7A.

FIGS. 7A and 7B illustrate one embodiment of a drill pin 700 for delivering a tissue fixation device such as tissue fixation devices 100, 300, 400, 500 described above. The drill pin 700 is generally an elongate structure having a proximal end 702 and a distal end having a tissue-penetrating tip (not shown) and a cavity 704 therein. The longitudinally oriented opening 708 leading to cavity 704 is defined at its lateral edges by sidewalls 706 and may be defined by an endwall 707 at its distal edge. There is no proximal boundary for the opening in the embodiment of FIGS. 7A and 7B.

With further reference to FIGS. 7A and 7B, the drill pin 700 has two longitudinally oriented openings 708 that are on opposite sides of the drill pin 700 and extend to the open proximal end 702 of the drill pin 700. That is, there is no proximal wall abutting the openings 708. In other embodiments, the drill pin 700 can have a single opening, or three or more openings. Multiple openings 708 can be positioned in any configuration along the circumference or outer edges of the drill pin 700, and the opening(s) 708 can have any suitable dimensions such that drill pin 700 is configured to enable deployment of a tissue fixation device through the opening 708 in the sidewall 706. Thus, generally, opening 708 is elongate and sized and shaped so that the tissue fixation device can be inserted into and delivered from opening 708.

Although shown to be at the proximal end of the drill pin 700, opening 708 can be located in any portion of the drill pin 700. For example, one or more openings can be positioned in a distal portion, a proximal portion, or a middle portion of the drill pin. In one embodiment, at least one opening is positioned in the proximal portion of the drill pin as shown, for example, in FIG. 7A.

The proximal end of the drill pin can have various configurations. For example, the proximal end of the drill pin 700 shown in FIG. 7A is open. In other embodiments, the proximal end of the drill pin can include a proximal end wall, which can be closed or which can possess one or more openings therein. In another aspect, the one or more openings in the proximal end wall can be in the form of an eyelet or slot or any other desired size or shape that is configured to accommodate passage of at least one graft retention loop coupled to the tissue fixation device during deployment of the tissue fixation device.

Figure 8A:
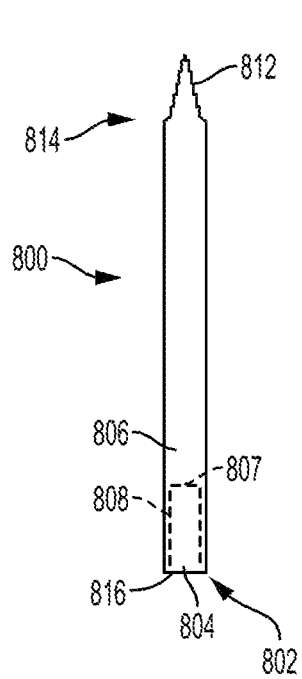
FIG. 8A is a side view of another embodiment of a drill pin having an opening in a sidewall thereof.
Figure 8B:
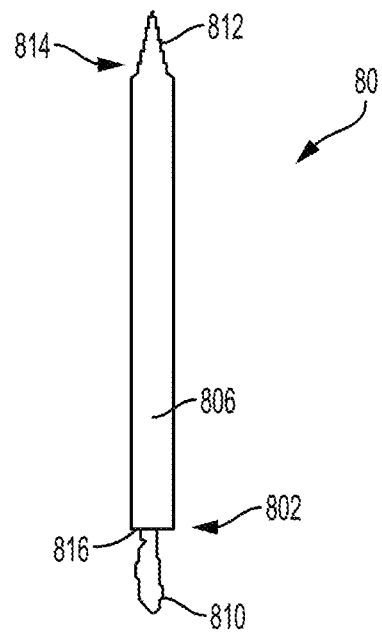
FIG. 8B is a side view of the of the drill pin of FIG. 8A with a tissue fixation device therein with a graft retention loop extending from the end thereof.

FIGS. 8A and 8B illustrate another embodiment of a drill pin 800 for delivering a tissue fixation device. As shown in FIGS. 8A and 8B, the drill pin 800 has a proximal end 802 and tissue-penetrating tip 812 at a distal end 814 thereof. Like the drill pin described above with respect to FIGS. 7A and 7B, drill pin 800 has a cavity 804 formed at least in the proximal end 802 thereof, and at least one longitudinally oriented opening 808 formed in sidewall 806 of the drill pin is in communication with cavity 804. Opening 808 is defined by lateral sidewalls 806, distal endwall 807, and proximal end wall 816 of the drill pin 800. In this embodiment, the proximal end wall 816 is partially open to accommodate the graft retention loop 810, which as shown in FIG. 8A, has a graft retention loop 810 extending through proximal endwall 816 from a tissue fixation device (not shown) contained in a cavity 804 of the drill pin 800. Like the drill pin described above with respect to FIGS. 7A and 7B, cavity 804 and opening 808 can also be positioned in the middle portion 816 of the drill pin or closer to the distal end of the drill pin. Moreover, drill pin 800 can have more than one opening 808 that communicates with cavity 804.

Figure 9A:
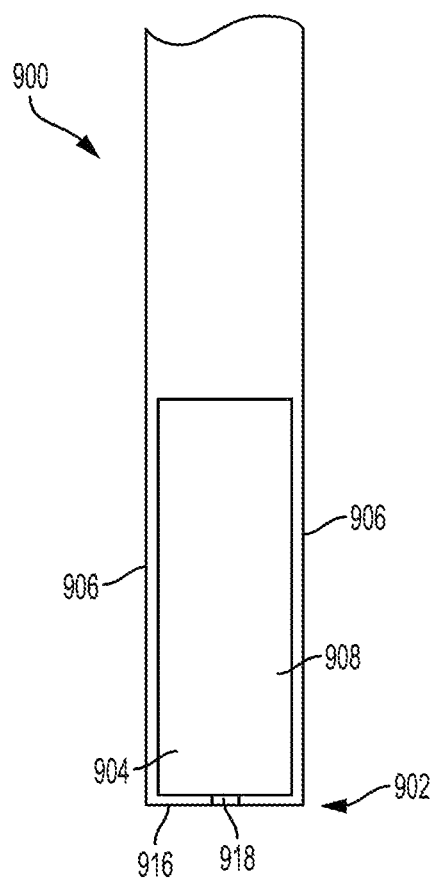
FIG. 9A is a side view of a portion of another embodiment of a drill pin having an opening therein.
Figure 9B:
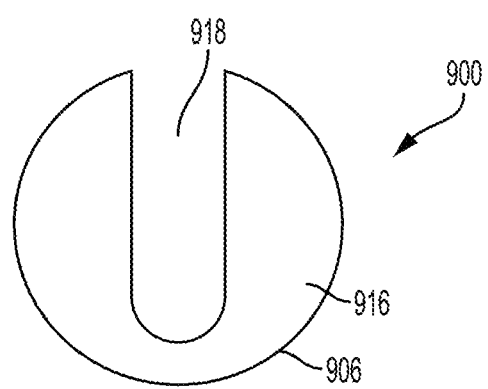
FIG. 9B is an end view of the drill pin of FIG. 9A showing a slot in the proximal end wall of the drill pin.

FIGS. 9A and 9B show yet another embodiment of a drill pin 900 in which an opening 908 in drill pin 900, in the form of a window in sidewall 906 of the drill pin 900, communicates with an internal cavity of the drill pin. Moreover, a proximal portion of the opening is defined by a proximal end wall 916. Like proximal end wall 816 of FIG. 8A, proximal end wall 916 of drill pin 900 is partially open. However, as shown in FIGS. 9A and 9B, proximal end wall 916 of has an opening in the form of slot 918 that communicates with opening 908, whereas opening 808 in sidewall 806 of FIG. 8A is not in communication with an opening in the proximal end wall 816.

Regardless of which variation of the drill pin is utilized, the tissue fixation device can be inserted into the drill pin in various ways. For example, the tissue fixation device can be inserted into the drill pin via the distal end, proximal end, or through the opening in the sidewall. In designs where the proximal end of the drill pin is open, the tissue fixation device can be inserted through the open proximal end. The tissue fixation device can also be angularly oriented and inserted into the cavity directly through the opening in the event that the tissue fixation device has a length that is greater than the length of the opening. The tissue device can also be deployed from the drill pin in similar manners, as described in more detail below.

FIGS. 10-17 show exemplary embodiments of tissue fixation devices at least partially seated within the drill pins of the type described herein. It is understood that FIGS. 10-17 are intended to generally illustrate the manner in which the tissue fixation devices is seated within the drill pins, but for ease of illustration the tissue fixation devices are shown to be spaced away from inner walls of the drill pin, a condition that is not likely to occur in reality.

Figure 10:
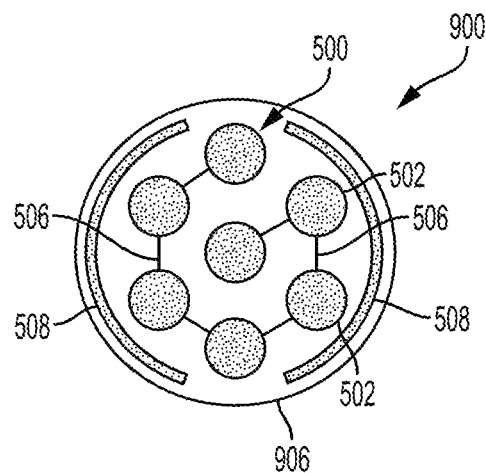
FIG. 10 is a proximal end view of an embodiment of a drill pin having a tissue fixation device therein.

FIG. 10 illustrates an embodiment of drill pin 900, viewed from its proximal end, having a tissue fixation device 500 disposed therein and configured in an unexpanded or delivery configuration and contained within cavity 904 of drill pin 900. Although not shown in FIG. 10, the sidewall 906 of the drill pin 900 has a longitudinal opening 908 formed therein as shown, for example, in FIG. 9A. In the illustrated embodiment the tissue fixation device 500 includes support members 502 connected by flexible members 506. Although tissue fixation device 500 is shown in FIG. 10 to have seven rigid support members 502, it is understood that the tissue fixation device 500 can include less than or more than seven support members 502. In the embodiment illustrated in FIG. 10, the graft retention loop 508 that is coupled to the tissue fixation device 500 is also contained within the cavity 904 of the drill pin 900. As explained below, however, other configurations can be used for the tissue fixation device and the drill pins.

Figure 11:
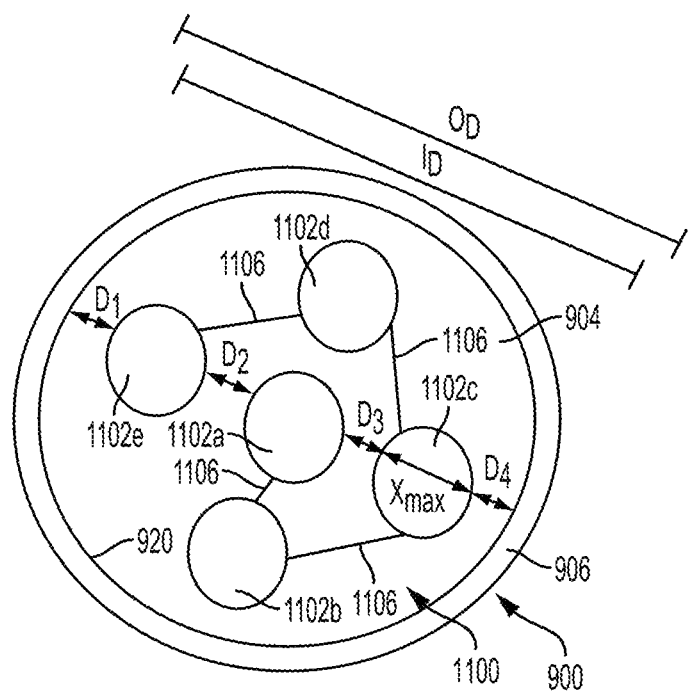
FIG. 11 is a proximal end view of another embodiment of a drill pin having a tissue fixation device therein, wherein the tissue fixation includes five rigid support members.

FIG. 11 illustrates another embodiment of a drill pin 900, viewed from its proximal end, having a tissue fixation device 1100 therein. As illustrated, tissue fixation device 1100 includes five rigid support members 1102a-1102e connected by flexible members 1106, and in FIG. 11 it is disposed in its delivery configuration as it is rolled up inside the drill pin 900.

When the tissue fixation device is disposed within the drill pin in a delivery configuration, the rigid support members are typically disposed in a non-intersecting orientation relative to one another. Thus, the rigid support members can be substantially parallel to one another. As so configured, the rigid support members are disposed a first distance away from one another that is less than a distance between the rigid support members in an uncompressed configuration. This reduced distance between substantially rigid support members allows the support members and flexible member coupled therebetween to have a reduced diameter so as to enable the tissue fixation device to be housed within the drill pin.

One skilled in the art will appreciate that dimensions of the drill pin and tissue fixation device can be any that are suitable for a desired application. Moreover, the dimensions of the tissue fixation device in its delivery configuration will depend on the dimensions of the drill pin through which it is delivered, and the dimensions of the tissue fixation device in its deployed configuration will depend on the requirements of the surgical procedure with which it is used and the anatomy in which it is placed. In one embodiment, the tissue fixation device has a length of about 12 mm, each rigid support member of the tissue fixation device has a diameter of about 0.5 mm, and the drill pin has an outer diameter of about 2.4 mm and an inner diameter of about 2 mm. The diameter of a widthwise cross-section of the support members of the tissue fixation device contributes to the overall size of the tissue fixation device and this dimension can vary. In the example of FIG. 11, the drill pin 900 has an inner diameter $I_D$ and an outer diameter $O_D$. In the illustrated delivery configuration, the three rigid support members 1102 e,a,c of the tissue fixation device 1100 are disposed within inner cavity 904 of drill pin 900 and extend along the length of the drill pin. As shown, rigid support members 1102 e,a,c are separated by each other and inner surface 920 of the sidewall 906 by distances $D_1$-$D_4$. The inner diameter of the drill pin should be large enough to accommodate the tissue fixation device in a clearance fit. In one embodiment, inner diameter $I_D$ can at least be equal to the sum of the distances $D_1$-$D_4$ between support members 1102e,a,c and inner surface 920 of sidewall 906 of drill pin 900 plus the number of rigid support members along a diameter of the drill pin multiplied by the maximum diameter of the rigid support member ($X_{max}$). In other words, $I_D=(D_1+D_2+D_3+D_4)+3(X_{max})$.

The length of the tissue fixation device can also vary. Although the length of the tissue fixation device is less than the length of the cavity of the drill pin, the length of the tissue fixation device can be greater than the length of an opening in the sidewall of the drill pin as long as the tissue fixation device can be inserted into the cavity when in the delivery configuration.

Figure 12A:
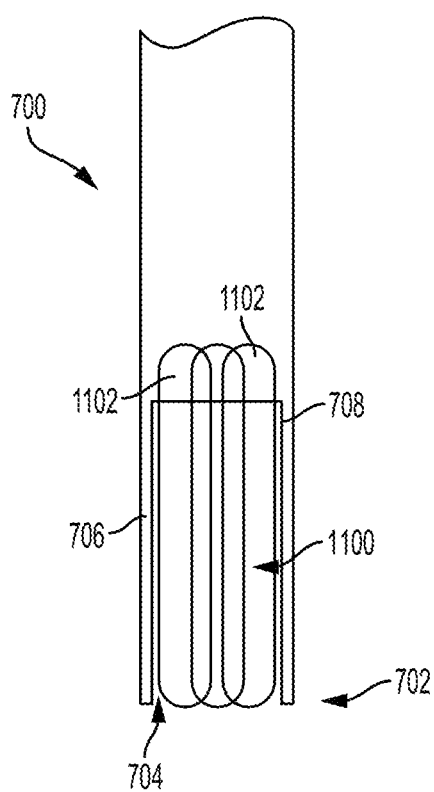
FIG. 12A is a partial schematic side view of the drill pin of FIG. 7A with a tissue fixation device therein.
Figure 12B:
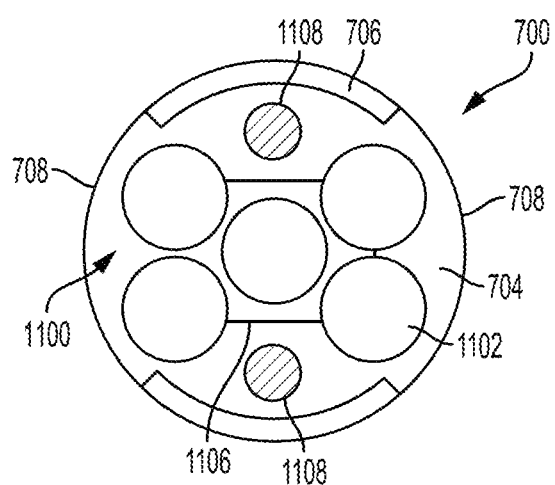
FIG. 12B is a schematic end view of the drill pin of FIG. 12A with the tissue fixation device therein.

FIGS. 12A and 12B illustrate an embodiment of drill pin 700 of FIGS. 7A and 7B having tissue fixation device 1100 of FIG. 11 disposed therein. In this embodiment, like FIGS. 7A and 7B, drill pin 700 has an open proximal end 702 with two longitudinal openings 708 in sidewall 706 of the drill pin, as shown in FIG. 12A. As explained above, sidewall 706 surrounds cavity 704 of the drill pin, and the longitudinally oriented openings 708 in the sidewall 706 are in communication with the cavity 704. As shown in FIG. 12A, drill pin 700 is configured to substantially contain therein the tissue fixation device 1100 when it is in the delivery configuration.

As shown in the proximal end view of the drill pin 700 in FIG. 12B, the tissue fixation device 1100 has five generally parallel rigid support members 1102 that are connected by flexible members 1106. In this embodiment, two legs of a graft retention loop 1108 are coupled to the tissue fixation device 1100 and are also shown in FIG. 12B. The tissue fixation device 1100 is shown in an unexpanded, delivery configuration within drill pin 700. In this undeployed configuration, the tissue fixation device 1100 has a diameter that is less than the diameter of the drill pin 700 so that it is able to fit within the drill pin in a clearance fit. Further, in this embodiment, the tissue fixation device 1100 has a length that is greater than the length of the openings 708 in the sidewall 706 of the drill pin 700. In other embodiments, however, the tissue fixation device 1100 can have a length that is the same as or less than the length of the opening 708 in the sidewall 706.

Figure 13:
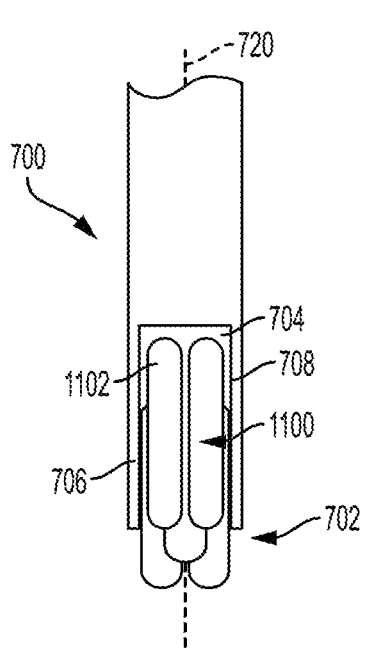
FIG. 13 is a schematic side view of the drill pin of FIG. 12A with the tissue fixation device partially deployed from the drill pin.
Figure 14:
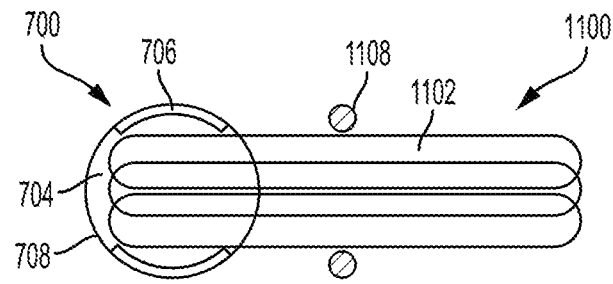
FIG. 14 is a schematic end view of the drill pin of FIG. 12A with the tissue fixation device partially deployed from the drill pin.
Figure 15:
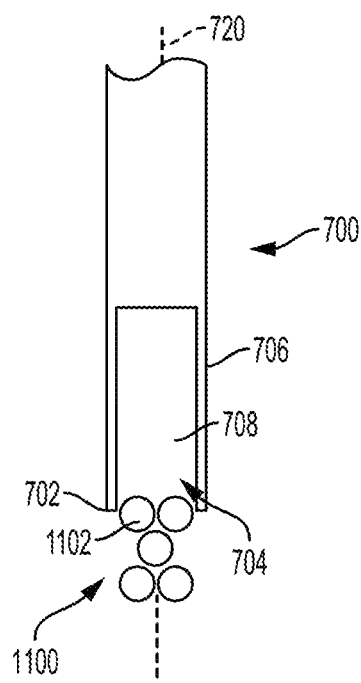
FIG. 15 is a schematic view of the drill pin of FIG. 12A with the tissue fixation device almost fully deployed through the end and opening in the sidewall of the drill pin.

FIGS. 13-15 illustrate an embodiment of tissue fixation device 1100 being partially deployed from drill pin 700, which is further illustrated in FIGS. 12A and 12B. As shown in FIG. 13, tissue fixation device 1100 is being partially deployed through opening 708 in sidewall 706 and the open proximal end 702 of drill pin 700. FIG. 14 shows tissue fixation device 1100 being partially deployed through the proximal end 702 of the drill pin of FIG. 12A. As shown, rigid support members 1102 are oriented at an angle such that they are not parallel to longitudinal axis 720 of drill pin 700 during the deployment process. In FIG. 15, tissue fixation device 1100 is almost fully deployed through proximal end 702 and opening 708 in sidewall 706 of drill pin 700. Only the ends of support members 1102 are shown in FIG. 15 as the tissue fixation device 1100 is oriented upon deployment so as to be generally perpendicular to longitudinal axis 720 of drill pin 700.

A person skilled in the art will appreciate that tissue fixation device 1100 can be deployed at various angles with respect to the longitudinal axis of the drill pin. In one embodiment, the tissue fixation device 1100 can be deployed through opening 708 in drill pin 700 at an angle so as to facilitate rotating the tissue fixation device 1100 into an orientation that is perpendicular to the drill pin so that the tissue fixation device spans a bone tunnel upon implantation. Tissue fixation device 1100 can also be deployed at an angle to prevent the tissue fixation device 1100 from entering the bone tunnel. Once the tissue fixation device is at least partially deployed, graft retention loop 1108 can be pulled to rotate the tissue fixation device 1100 into a desired final position. A person skilled in the art will appreciate that other suitable methods of creating a downward force can be employed to facilitate rotation of the tissue fixation device 1100 during deployment.

Figure 16:
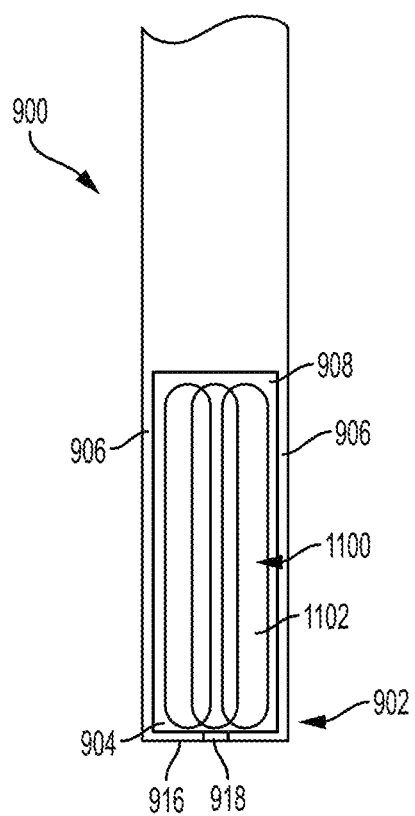
FIG. 16 is a schematic side view of an embodiment of the drill pin of FIG. 9A having an end surface with a slot therein and a tissue fixation device seated in the cavity of the drill pin.
Figure 17:
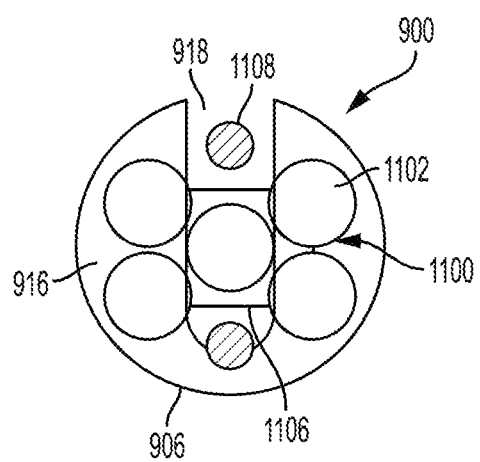
FIG. 17 is a schematic end view of the drill pin and tissue fixation device of FIG. 16.

FIGS. 16 and 17 show another embodiment of tissue fixation device 1100 disposed in drill pin 900, which is a drill pin of the type illustrated in FIGS. 9A and 9B having a proximal end wall 916 with a slot 918 therein. As shown in FIG. 16, tissue fixation device 1100 has a length that is less than the length of opening 908 in sidewall 906 of drill pin 900 and when the tissue fixation device is in its rolled, unexpanded configuration within the drill pin it has a diameter that is less than the inner diameter of drill pin 900. Thus, in its unexpanded configuration, tissue fixation device 1100 can easily be inserted through opening 908 in sidewall 906 and into cavity 904 of the drill pin. Because slot 918 in the proximal end 902 of drill pin 900 is not sufficiently large for deployment of the tissue fixation device therethrough, tissue fixation device 1100 can only be deployed through opening 908 in sidewall 906 for the embodiment of FIGS. 16 and 17. During deployment of tissue fixation device 1100 from drill pin 900, at least one graft retention loop 1108 can pass through slot 918 while tissue fixation device 1100 can pass through opening 908 in sidewall 906, which is in communication with the slot 918. As discussed above with respect to FIGS. 13-15, tissue fixation device 1100 can likewise be deployed from drill pin 900 at an angle to facilitate rotating the tissue fixation device 1100 into the perpendicular orientation relative to the longitudinal axis of the drill pin so that the tissue fixation device lies across a bone tunnel following implantation.

Some embodiments provide a method for fixating a graft ligament within a bone tunnel using the tissue fixation device and the drill pins described herein. In one embodiment, the method generally includes forming a graft construct by coupling the graft or graft ligament to a tissue fixation device via a graft retention loop of the tissue fixation device. Any suitable tissue fixation device and graft including those disclosed herein may be used to form the graft construct. The method also includes utilizing a drill pin of the type shown, for example, in the embodiments of FIGS. 7A-9B that has a tissue fixation device disposed in a cavity of the drill pin in a collapsed, delivery configuration. During such a procedure the drill pin is embedded into a bone to form a bone tunnel, the tissue fixation device is deployed through the opening in the drill pin, and the graft construct is passed through the bone tunnel with the tissue fixation device in the delivery configuration, and the tissue fixation device is positioned over a first end of the bone tunnel in a deployed configuration. These steps can be performed in any suitable order. For example, in one embodiment described below, the graft can be coupled to the tissue fixation device via the graft retention loop after formation of the bone tunnel.

The methods described herein can be used in various surgical procedures including, for example, ligament reconstruction surgery involving fixation of anterior or posterior cruciate ligaments. The disclosed techniques can be adapted for other surgical procedures as well. For example, the described devices and methods can be used for acromioclavicular joint reconstruction and ankle syndesmosis. The devices and methods can be used for anastomosis and other surgeries where it is required to bring together two (or more) soft tissues, soft tissue and bone tissue, or two bone tissues need to be brought or held together.

Figure 18:
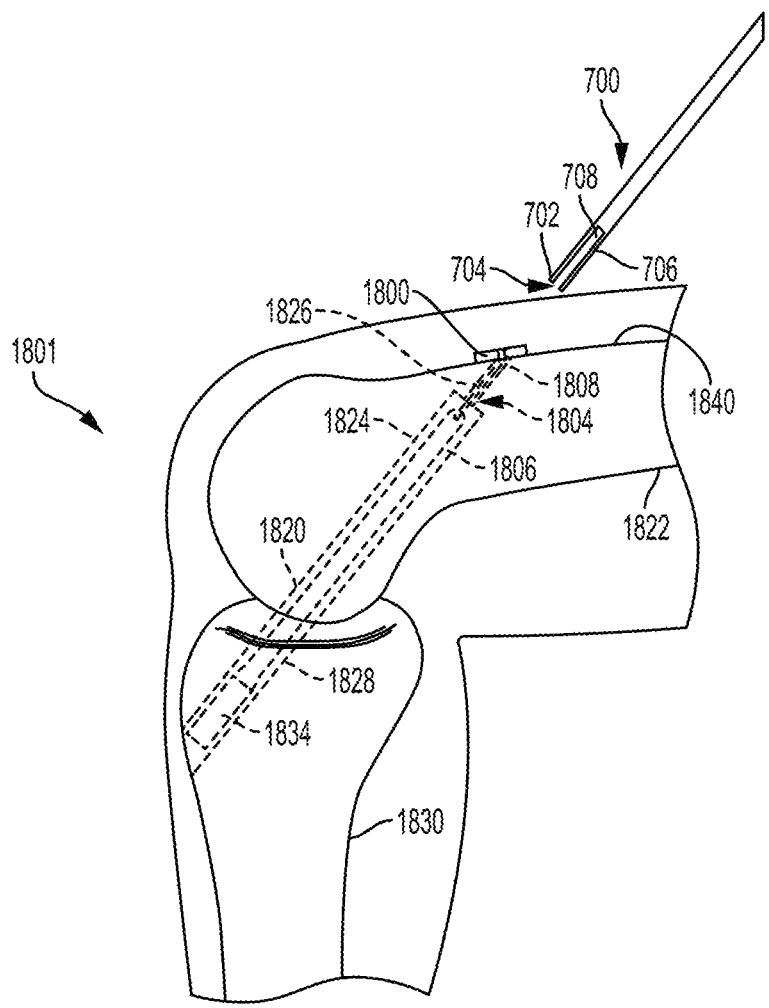
FIG. 18 is a side elevation cross-sectional view of a knee having an ACL reconstruction procedure using a tissue fixation device and the drill pin of FIG. 7A.

FIGS. 18 and 19A-G illustrate the use of the drill pin and tissue fixation devices described herein in a ligament reconstruction surgery involving fixation of the anterior cruciate ligament. FIG. 18 illustrates a patient's leg 1801 in the course of an ACL reconstruction procedure performed thereon using a tissue fixation device 1800, such as tissue fixation device 100 (FIGS. 1A, 1B, 2A, and 2B) or tissue fixation device 300 (FIGS. 3A and 3B), and drill pin 700 (FIGS. 7A and 7B). In some embodiments, other drill pins such as drill pins 800, 900, described above, can be used in accordance with this method. FIG. 18 shows tissue fixation device 1800 deployed on the lateral femoral cortex 1840 and a graft or graft tendon 1806 disposed in femoral bone socket 1824 and tibial bone tunnel 1828.

Surgical techniques for ligament reconstruction are well known. Generally, the method includes forming a bone tunnel to receive the graft tendon 1806 therein. A bone tunnel for an ACL reconstruction procedure in a patient's leg can be formed by drilling a tibial tunnel through the tibia, as known in the art. A femoral tunnel is then drilled such that the diameters of the femoral and tibial tunnels are appropriate to snugly fit the graft construct therethrough. In the embodiments described herein, because of the smaller size of tissue fixation device 1800 itself as well as drill pin 700 containing the tissue fixation device 1800 as compared to existing devices, a passing tunnel having a diameter that is less than a diameter of a passing tunnel required to pass therethrough a conventional device can be formed.

In the illustrated embodiment, as shown in FIGS. 18, 19A, 19B, and 19C, a bone tunnel 1820 in the patient's leg 1801 is formed that includes a femoral tunnel or socket 1824 and a tibial bone tunnel 1828. In the illustrated embodiment, a drill pin 700 is used to drill a relatively small diameter bone tunnel through the femur 1822. A diameter of such bone tunnel drilled using the drill pin 700 can be in the range of about 1 mm to about 5 mm. In one embodiment, the tunnel diameter is about 2.4 mm. This step forms a passing bone tunnel 1826 shown in FIGS. 18, 19A, and 19B that extends from the condylar notch of the femur laterally to the lateral cortex.

Figures 19A, 19B, 19C:
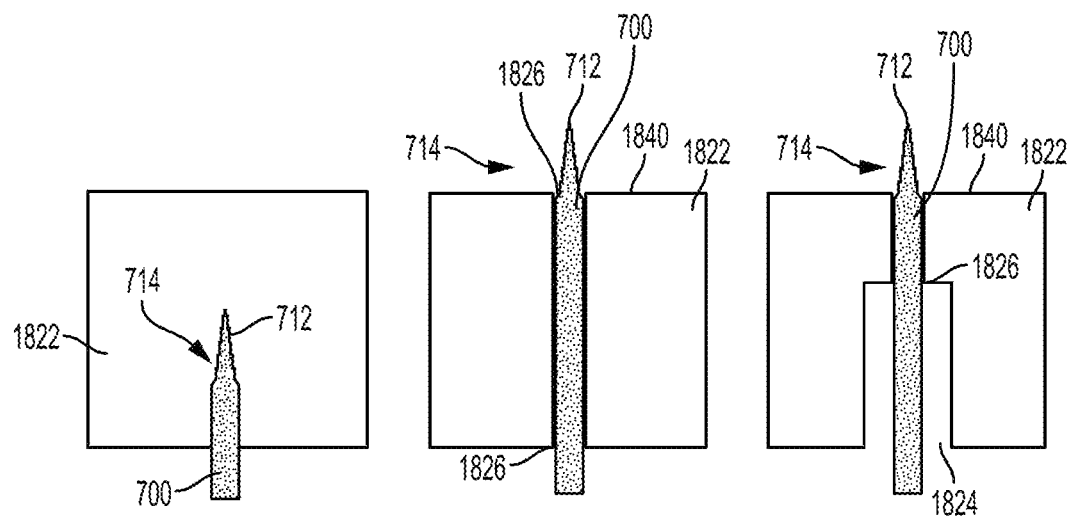
FIGS. 19A-19G are sequential side cross-sectional views of an embodiment of a drill pin and a tissue fixation device being deployed to a bone during a surgical procedure.

FIGS. 19A and 19B generally show an enlarged view of drill pin 700 forming femoral bone tunnel 1826. FIG. 19A shows the tissue penetrating tip 712 at the distal end 714 of the drill pin 700 being introduced into a bone such as femur 1822, shown in FIG. 18, to form bone tunnel 1826. Drill pin 700 has tissue fixation device 1800 seated therein at its proximal end (not shown). FIG. 19B shows drill pin 700 inserted a further distance into the bone and through the opposite side, e.g., the lateral cortex 1840, of the femur 1822 to complete bone tunnel 1826.

Next, the larger diameter femoral bone socket 1824 can be formed through the femur 1822, sized so as to receive the graft tendon 1806 therein. The femoral bone tunnel 1826 can be formed using, for example, a cannulated drill or reamer advanced over the drill pin 700, or using any other suitable technique. The drill pin 700 can remain in the bone tunnel 1826 during formation of the femoral bone socket 1824. FIG. 19C shows drill pin 700 extending through bone tunnel 1826 with a femoral bone socket 1824 formed in a portion of the femur 1822 closer to the proximal end of the drill pin 700. FIG. 18 illustrates a tunnel 1820 in femur 1822 including femoral bone socket 1824 sized to accommodate graft tendon 1806 and a smaller diameter superior portion or passing channel or bone tunnel 1826 formed by drill pin 700 that houses tissue fixation device 1800 in a delivery configuration. The diameter of the femoral bone socket 1824 can be in the range of about 6 to about 12 mm. In one embodiment, the diameter of the femoral bone socket 1824 is about 9 mm.

Once the femoral bone socket 1824 is created, the formation of the bone tunnel for the procedure is complete. As indicated above, the passing bone tunnel 1826 is formed in the femur superiorly to the femoral bone socket 1824 by drilling the drill pin 700 through the femur. Thus, it is not required to form a separate passing tunnel. In contrast, a technique using a conventional tissue fixation device without the drill pin 700 described herein would require an additional step of forming a larger passing tunnel having a diameter of about 4.5 mm. With the techniques described herein, the passing bone tunnel 1826 can have a diameter in the range of about 2.4 mm to about 4.4 mm, for example, which corresponds to an outer diameter of a drill pin used to form the passing bone tunnel 1826.

The above steps can be applied when the tissue fixation device is delivered via a transtibial (TT) portal approach which can be used, for example, when delivering a tissue fixation device having a fixed or adjustable graft retention loop. In the TT portal approach, as discussed above, a tibial tunnel can be drilled in a desired manner. The drill pin described herein can then be drilled into the femur at a desired location via the tibial tunnel, as generally shown in FIGS. 19A and 19B.

Figures 19D, 19E:
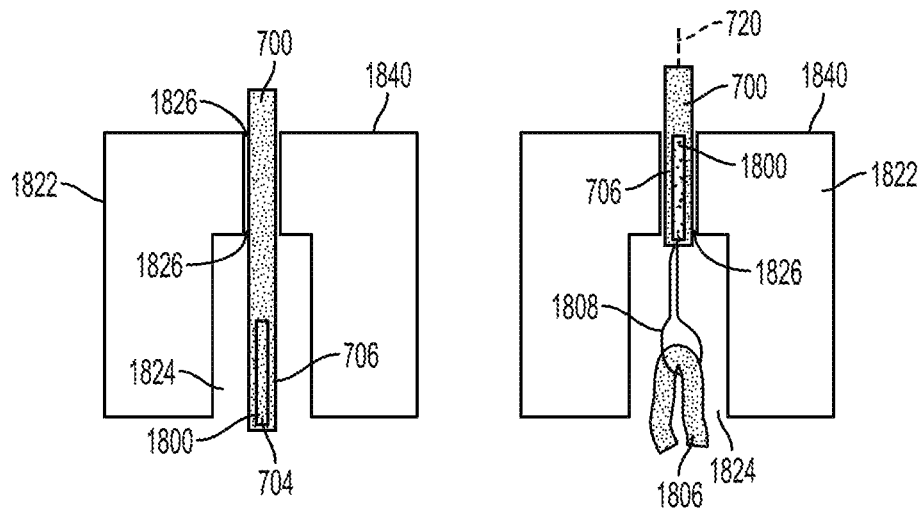

In another embodiment, tissue fixation device 1800 can be delivered via an anteromedial (AM) portal approach which can be used, for example, when delivering the tissue fixation device with an adjustable graft retention loop 1808. The AM portal approach involves first drilling drill pin 700 into femur 1822 at the center of the ACL footprint or at another desired location via the AM portal and then drilling a tibial bone tunnel 1828 into tibia 1830. The bone tunnel 1826 can be formed in the femur as described above and shown in FIGS. 19A and 19B. After bone tunnel 1826 is formed, the drill pin can then be overdrilled to a desired distance, leaving adequate bone shelf laterally to form femoral bone socket 1824 as shown in FIG. 19C. Drill pin 700 can then be advanced further into femur 1822 until the proximal end of the drill pin containing tissue fixation device 1800 rests inside femoral bone tunnel 1826, as shown in FIG. 19D. Drill pin 700 can remain in bone tunnel 1826 as tibial bone tunnel 1828 shown in FIG. 18 is drilled using any suitable technique.

Drill pin 700 can then be moved in a retrograde manner to exit the knee joint via the AM portal. Graft retention loop 1808, which is coupled to the tissue fixation device 1800, can then be extended from tissue fixation device 1800 out of drill pin 700 and into the femoral bone socket 1824, as shown in FIG. 19E.

Next, drill pin 700 can be advanced further through femur 1822 until graft retention loop 1808 is accessible in a joint. An arthroscopic grasper or another suitable tool can be used to pull graft retention loop 1808 inferiorly through tibial bone tunnel 1828. Graft tendon 1806 can then be loaded onto the graft retention loop 1808, as shown in FIG. 19E. Graft tendon 1806 can be loaded in any suitable manner, including by techniques described herein. For example, as understood by a person skilled in the art, graft construct 1804 can be formed by coupling graft tendon 1806 to tissue fixation device 1800 via graft retention loop 1808 of tissue fixation device 1800. This can be done after bone tunnel 1820 and femoral bone socket 1824 are formed.

Once graft 1806 is loaded on graft retention loop 1808 (using the AM or TT portal approach or any other suitable method), as shown in FIG. 19E, drill pin 700 can be advanced further into femur 1822 so that graft 1806 passes through tibial bone tunnel 1828 and joint space, and into femoral bone socket 1824, as generally shown in FIGS. 19D and 19E. FIG. 19D shows the proximal end of drill pin 700 in femoral bone socket 1824 with tissue fixation device 1800 seated in cavity 704 of drill pin 700. FIG. 19E illustrates the proximal end 702 of drill pin 700 and tissue fixation device 1800 advanced further into femur 1822 with graft retention loop 1808 and a portion of graft 1806 in femoral bone socket 1824.

Figure 19F:
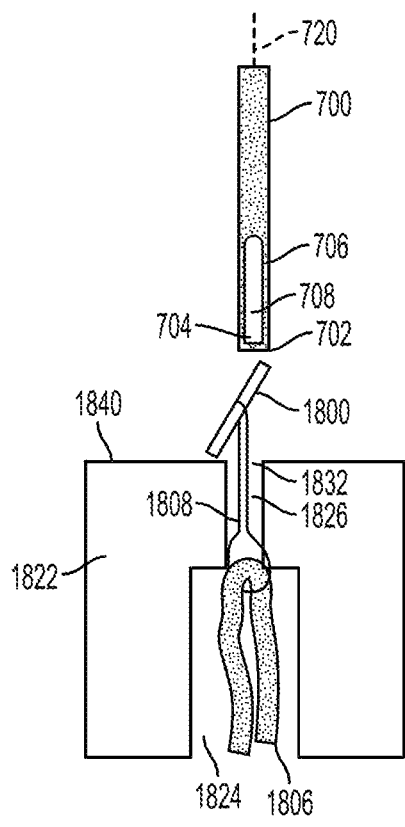

As shown in FIG. 19F, drill pin 700 is advanced through bone tunnel 1826 until tissue fixation device 1800 contained therein extends beyond femoral cortex 1840 above an opening 1832 of passing bone tunnel 1826. Drill pin 700 can be pulled through the bone tunnel 1826 using a pin puller or other suitable instrument.

When the proximal end of drill pin containing the tissue fixation device has passed through the lateral cortex 1840, as shown in FIG. 19F, tissue fixation device 1800 can be released from the drill pin 700 and the drill pin 700 can be removed from the femoral cortex 1840. In one embodiment, a loop adjustment suture (not shown) can exit the skin with the drill pin. In another embodiment, the loop adjustment suture can trail down past the graft and through the tibial bone tunnel.

In this embodiment, tissue fixation device 1800 is deployed through opening 708 in drill pin 700 as graft 1806 is pulled through the femoral bone socket 1824 to opening 1832 of bone tunnel 1826. Tissue fixation device 1800 is deployed from cavity 704 of drill pin 700 at an angle with respect to longitudinal axis 720 of drill pin 700.

In embodiments where the drill pin has a slot on the end surface thereof, graft retention loop 1808 can extend through the slot and pass through the slot as tissue fixation device 1800 is deployed.

Tissue fixation device 1800 is deployed by pulling on graft retention loop 1808 that connects drill pin 700 to graft 1806. Tissue fixation device 1800 can be released from drill pin 700 when significant resistance is felt which indicates that graft 1806 is fully engaged with the top of femoral bone socket 1824. At this point, tissue fixation device 1800 is in a position to exit femoral cortex 1840 and drill pin 700 can then be pulled out of femur 1822, as shown in FIG. 19F. In one embodiment, the connection of drill pin 700 and tissue fixation device 1800 can be configured such that tissue fixation device 1800 automatically disengages from drill pin 700 at a specific tensile load.

In another embodiment, cavity 704 can be closer to the middle of drill pin 700 with respect to longitudinal axis 720 of drill pin 700. Cavity 704 can be positioned such that the proximal end of drill pin 700 is positioned at the entrance to the femoral tunnel prior to deploying tissue fixation device 1800 from drill pin 700.

In some embodiments, cavity 704 of drill pin 700 need not communicate with an opening in sidewall 706 of drill pin 700. In fact, drill pin 700 need not have any openings in sidewall 706 of drill pin 700 and instead cavity 704 communicates only with an opening at the proximal end of drill pin 700. Drill pin 700 can be sized so that there is a sufficient retention force to hold tissue fixation device 1800 in place, but not dislodge the tissue fixation device 1800 when a pulling force is applied to drill pin 700.

Figure 19G:
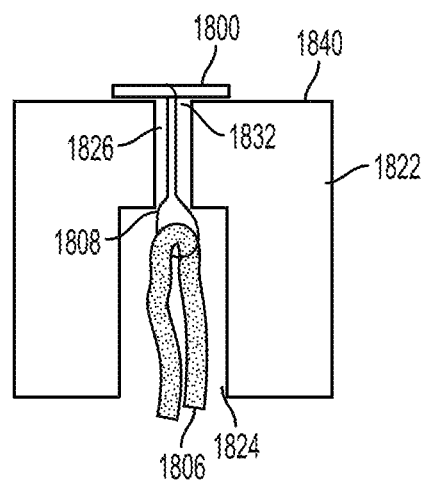

Upon deployment, tissue fixation device 1800 is "flipped" such it is positioned over and across opening 1832, as shown in FIG. 19G. The tissue fixation device can be flipped in any suitable manner that moves the tissue fixation device from an angled position as shown in FIG. 19F to the position shown in FIG. 19G that is generally parallel to the surface of femur 1822. For example, tension can be applied to a suture (not shown). Creating a downward force vector, particularly one that is non-parallel to the longitudinal axis of the drill pin, can facilitate maneuvering the tissue fixation device.

As shown in FIG. 19G, in the deployed configuration, graft retention loop 1808 with graft 1806 coupled thereto extend into bone tunnel 1826. As explained above, when tissue fixation device 1800 is in the deployed configuration, it is generally perpendicular with respect to the first end of bone tunnel 1826. Also, the rigid support members (such as support member 102, 104 shown in FIGS. 1A and 1B) of the tissue fixation device 1800 are disposed a second distance away from one another that can be greater than the first distance between the rigid support members when they are in the delivery configuration. In the deployed configuration, the rigid support members remain disposed in the non-intersecting orientation relative to one another.

While the distance between the rigid support members in the deployed configuration is greater than that in the delivery configuration, the distance between the rigid support members in the deployed configuration can be less than a distance between the rigid support members in the uncompressed configuration of the tissue fixation device 1800. Tension applied to graft 1806 during the procedure causes tension to be also applied to tissue fixation device 1800 such that the rigid support members tend to move closer together. It is to be understood that the flexible members can be in a configuration (e.g., compressed, deformed, folded, crimped, etc.) that is different from its uncompressed configuration so as to allow the distance between the rigid support members to decrease relative to that in the uncompressed configuration. However, in some embodiments, the distance between the rigid support members in the deployed configuration can be the same as that in the uncompressed configuration of tissue fixation device 1800.

The support members can be in any orientation when they are positioned over opening 1832, however they generally do not intersect. Although the support members are substantially rigid, they can have some degree of flexibility or malleability such that tissue fixation device 1800 can be positioned over opening 1832 so as to conform to the shape of the lateral cortex. In this way, tissue fixation device 1800, once implanted, can be less palpable as compared to existing devices. In the deployed configuration, as shown in FIG. 19G, tissue fixation device 1800 sits on femur 1822 in a sideways orientation with graft retention loop 1808 and graft 1806 extending medially through passing bone tunnel 1826 and into socket 1824. Graft retention loop 1808 passes around both sides of tissue fixation device 1800 such that it is supported by both the support members. However, in some cases, the graft retention loop can pass over one side of the device so as to be supported by one of the support members. An opposite end of graft 1806 can be placed into a tibial bone tunnel 1828 in the leg's tibia 1830 and held in place with a suitable anchor 1834. After tissue fixation device 1800 is implanted, any leading and trailing sutures can be removed.

Graft 1806 can be held in place within bone socket 1824 by graft retention loop 1808. In one embodiment, graft retention loop 1808 can be of a fixed length. Another embodiment can include a loop adjustment suture that can exit the skin with drill pin 700, or can trail past graft 1806 and through tibial bone tunnel 1828. For adjustable loop tissue fixation devices, a loop adjustment suture can be pulled until graft 1806 is fully engaged with the femoral tunnel and tissue fixation device 1800 is resting on the lateral cortex of femur 1822, as shown in FIGS. 18 and 19G.

After deployment of tissue fixation device 1800 and graft 1806 in bone socket 1824, a tibial fixation can then be performed in any desired manner. An end of graft 1806 opposite bone socket 1824 can be placed into a tibial bone tunnel 1828 in the leg's tibia and held in place with a suitable anchor 1834.

It is understood that graft tendon 1806 can be any suitable type of graft. For example, an autograft, which is a portion of the patient's own tissue that would replace the damaged natural ligament, can be used. The autograft is often a hamstring tendon, though other tendons can be used (e.g., a patellar tendon). The tendon graft can also be an allograft obtained from a donor. The graft tendon can be prepared in a suitable manner well known to those skilled in the art, which can involve cleaning and measuring the graft, and then reinforcing free ends thereof.

It is also to be understood that in various figures graft tendon 1806 is not shown to scale as the graft tendon actually has thicker dimensions such that it substantially entirely fills the bone tunnel (e.g., femoral bone socket 1824) in which it is received. Graft tendon 1806, once implanted, contacts the bone in which the bone tunnel is formed such that graft 1806 grows into and merges with the bone for a permanent repair.

It should be appreciated that although illustrated embodiments provide systems, devices, and methods for orthopedic surgeries, such as, for example, ligament reconstruction surgery involving fixation of anterior or posterior cruciate ligaments, the techniques can be adapted for other surgical procedures as well. For example, the described devices and methods can be used for acromioclavicular joint reconstruction and ankle syndesmosis. The devices and methods can be used for anastomosis and other surgeries where it is required to bring together two (or more) soft tissues, soft tissue and bone tissue, or two bone tissues need to be brought or held together.

Having thus described some examples of the described embodiments, various alterations, modifications, and improvements will readily occur to those skilled in the art. Such alterations, modifications, and improvements are intended to be within the spirit and scope of the described embodiments. Accordingly, the foregoing description is by way of example only, and not intended to be limiting.

What is claimed is:

1. A method for fixating a graft ligament, comprising:
   forming a graft construct by coupling the graft ligament to a tissue fixation device via a graft retention loop of the tissue fixation device, the tissue fixation device comprising a first rigid support member and a second rigid support member, the first rigid support member and the second rigid support member each being a discrete element and separated from each other by at least one flexible member connecting the first rigid support member and the second rigid support member;
   inserting the tissue fixation device in a, delivery configuration into a cavity at a proximal end of a drill pin, the cavity defined by a sidewall surrounding at least part of the cavity, the cavity being configured to contain the tissue fixation device therein;
   drilling the drill pin into a bone to form a bone tunnel that passes entirely through the bone;
   passing the tissue fixation device through the bone tunnel with the tissue fixation device in the delivery configuration;
   deploying the tissue fixation device through an opening in the drill pin; and
   positioning the tissue fixation device over a first end of the bone tunnel in a deployed configuration such that the first rigid support member and the second rigid support member are spaced from one another by a distance greater than in the delivery configuration, and the graft retention loop and the graft ligament extend into the bone tunnel.

2. The method of claim 1, wherein the drill pin has a proximal end surface in communication with the sidewall, wherein the proximal end surface of the drill pin has a slot located therein, wherein the slot is in communication with the opening, and wherein prior to deployment of the tissue fixation device, the at least one graft retention loop passes through the slot.

3. The method of claim 1, further comprising pulling the drill pin through the bone tunnel.

4. The method of claim 3, wherein the drill pin is pulled using a pin puller.

5. The method of claim 1, wherein, when in the deployed configuration, the tissue fixation device is generally perpendicular with respect to the first end of the bone tunnel.

6. The method of claim 1, wherein the drill pin has a longitudinal axis, and the tissue fixation device is deployed through the opening at an angle with respect to the longitudinal axis.

7. The method of claim 1, wherein the at least one flexible member comprises a plurality of elongate connecting filaments extending between the first rigid support member and the second rigid support member.

8. The method of claim 1, wherein the tissue fixation device is collapsed in the delivery configuration.

9. A method for fixating a graft ligament, comprising:

forming a graft construct by coupling the graft ligament to a tissue fixation device via a graft retention loop of the tissue fixation device, the tissue fixation device comprising a first rigid support member and a second rigid support member, the first rigid support member and the second rigid support member each being a discrete element and separated from each other by at least one flexible member connecting the first rigid support member and the second rigid support member;

inserting the tissue fixation device in a, delivery configuration into a cavity at a proximal end of a drill pin, the cavity defined by a sidewall surrounding at least part of the cavity, the cavity being configured to contain the tissue fixation device therein;

drilling the drill pin into a bone to form a bone tunnel;

passing the tissue fixation device through the bone tunnel with the tissue fixation device in the delivery configuration;

deploying the tissue fixation device through an opening in the drill pin; and positioning the tissue fixation device over a first end of the bone tunnel in a deployed configuration such that the first rigid support member and the second rigid support member are spaced from one another by a distance greater than in the delivery configuration, the graft retention loop and the graft ligament extend into a socket formed in the bone and disposed proximate a second end of the bone tunnel, the second end opposite the first end, and the graft ligament fills the socket.

10. The method of claim 9, wherein the drill pin has a proximal end surface in communication with the sidewall, wherein the proximal end surface of the drill pin has a slot located therein, wherein the slot is in communication with the opening, and wherein prior to deployment of the tissue fixation device, the at least one graft retention loop passes through the slot.

11. The method of claim 9, further comprising pulling the drill pin through the bone tunnel.

12. The method of claim 11, wherein the drill pin is pulled using a pin puller.

13. The method of claim 9, wherein, when in the deployed configuration, the tissue fixation device is generally perpendicular with respect to the first end of the bone tunnel.

14. The method of claim 9, wherein the drill pin has a longitudinal axis, and the tissue fixation device is deployed through the opening at an angle with respect to the longitudinal axis.

15. The method of claim 9, wherein the at least one flexible member comprises a plurality of elongate connecting filaments extending between the first rigid support member and the second rigid support member.

16. The method of claim 9, wherein the tissue fixation device is collapsed in the delivery configuration.

* * * * *